United States Patent
Germain et al.

(10) Patent No.: US 11,712,291 B2
(45) Date of Patent: Aug. 1, 2023

(54) ARTHROSCOPIC DEVICES AND METHODS

(71) Applicant: Relign Corporation, Campbell, CA (US)

(72) Inventors: Aaron Germain, San Jose, CA (US); Jacob Tonkel, San Jose, CA (US); Jan Echeverry, San Jose, CA (US)

(73) Assignee: Relign Corporation, Campbell, CA (US)

( * ) Notice: Subject to any disclaimer, the term of this patent is extended or adjusted under 35 U.S.C. 154(b) by 209 days.

(21) Appl. No.: 17/351,661

(22) Filed: Jun. 18, 2021

(65) Prior Publication Data

US 2021/0346080 A1 Nov. 11, 2021

Related U.S. Application Data

(63) Continuation of application No. 16/392,257, filed on Apr. 23, 2019, now Pat. No. 11,058,480.

(60) Provisional application No. 62/663,877, filed on Apr. 27, 2018.

(51) Int. Cl.
*A61B 18/14* (2006.01)
*A61B 17/32* (2006.01)
*A61B 17/16* (2006.01)
*A61B 18/00* (2006.01)
*A61B 17/00* (2006.01)

(52) U.S. Cl.
CPC ........ *A61B 18/148* (2013.01); *A61B 17/1615* (2013.01); *A61B 17/32002* (2013.01); *A61B 17/1628* (2013.01); *A61B 17/1633* (2013.01); *A61B 2017/0046* (2013.01); *A61B 2018/00577* (2013.01); *A61B 2018/00589* (2013.01); *A61B 2018/00601* (2013.01)

(58) Field of Classification Search
CPC combination set(s) only.
See application file for complete search history.

(56) References Cited

U.S. PATENT DOCUMENTS

| | | | |
|---|---|---|---|
| 4,532,924 A | 8/1985 | Auth et al. | |
| 8,221,404 B2 | 7/2012 | Truckai | |
| 8,323,280 B2 | 12/2012 | Germain et al. | |
| 9,204,918 B2 | 12/2015 | Germain et al. | |
| 9,247,983 B2 | 2/2016 | Truckai et al. | |

(Continued)

FOREIGN PATENT DOCUMENTS

WO WO-2019210004 A1 10/2019

OTHER PUBLICATIONS

U.S. Appl. No. 16/392,257, filed Apr. 23, 2019, Arthroscopic Devices and Methods.

(Continued)

*Primary Examiner* — Sameh R Boles
(74) *Attorney, Agent, or Firm* — Schwegman Lundberg & Woessner, P.A.

(57) ABSTRACT

An arthroscopic cutting probe includes a shaft assembly having a distal end, a proximal end, and a longitudinal axis. A distal cutting member is rotatably attached at the distal end of the shaft assembly, and at least a portion of an exterior surface of the distal cutting member is electrically insulated. One or more burr elements extend radially outwardly from the electrically insulated portion of the exterior surface of the distal cutting member, wherein the burr element is electrically conductive to form an active electrode.

20 Claims, 18 Drawing Sheets

(56) References Cited

U.S. PATENT DOCUMENTS

| | | |
|---|---|---|
| 9,277,954 B2 | 3/2016 | Germain et al. |
| 9,585,675 B1 | 3/2017 | Germain et al. |
| 9,592,085 B2 | 3/2017 | Germain et al. |
| 9,603,656 B1 | 3/2017 | Germain et al. |
| 9,681,913 B2 | 6/2017 | Orczy-timko et al. |
| 9,795,434 B2 | 10/2017 | Germain et al. |
| 9,855,675 B1 | 1/2018 | Germain et al. |
| 10,022,140 B2 | 7/2018 | Germain et al. |
| 10,028,767 B2 | 7/2018 | Germain et al. |
| 10,052,149 B2 | 8/2018 | Germain et al. |
| 10,595,889 B2 | 3/2020 | Germain et al. |
| 2016/0113706 A1 | 4/2016 | Truckai et al. |
| 2016/0157916 A1 | 6/2016 | Germain et al. |
| 2016/0184008 A1 | 6/2016 | Papaioannou et al. |
| 2017/0128083 A1 | 5/2017 | Germain et al. |
| 2017/0172648 A1 | 6/2017 | Germain et al. |
| 2017/0181754 A1 | 6/2017 | Loreth |
| 2017/0202612 A1* | 7/2017 | Germain .......... A61B 17/32002 |
| 2017/0252099 A1 | 9/2017 | Orczy-Timko et al. |
| 2017/0258512 A1 | 9/2017 | Germain et al. |
| 2017/0258519 A1 | 9/2017 | Germain et al. |
| 2017/0290602 A1 | 10/2017 | Germain et al. |
| 2017/0303990 A1 | 10/2017 | Benamou et al. |
| 2018/0000534 A1 | 1/2018 | Germain et al. |
| 2018/0008334 A1 | 1/2018 | Germain et al. |
| 2018/0093391 A1 | 4/2018 | Germain et al. |
| 2018/0161088 A1 | 6/2018 | Poser et al. |
| 2018/0263649 A1 | 9/2018 | Germain et al. |
| 2018/0303509 A1 | 10/2018 | Germain et al. |
| 2018/0317957 A1 | 11/2018 | Germain et al. |
| 2019/0008538 A1 | 1/2019 | Germain et al. |
| 2019/0008541 A1 | 1/2019 | Norton et al. |
| 2019/0015151 A1 | 1/2019 | Germain et al. |
| 2019/0021788 A1 | 1/2019 | Germain et al. |
| 2019/0059983 A1 | 2/2019 | Germain et al. |
| 2019/0083121 A1 | 3/2019 | Benamou et al. |
| 2019/0328448 A1 | 10/2019 | Germain et al. |

OTHER PUBLICATIONS

"U.S. Appl. No. 16/392,257, Non Final Office Action dated Jan. 21, 2021", 11 pgs.

"U.S. Appl. No. 16/392,257, Notice of Allowance dated Mar. 16, 2021", 5 pgs.

"U.S. Appl. No. 16/392,257, Response filed Jan. 12, 2021 to Restriction Requirement dated Sep. 16, 2020", 6 pgs.

"U.S. Appl. No. 16/392,257, Response filed Feb. 24, 2021 to Non Final Office Action dated Jan. 21, 2021", 8 pgs.

"U.S. Appl. No. 16/392,257, Restriction Requirement dated Sep. 16, 2020", 10 pgs.

"International Application Serial No. PCT/US2019/028997, International Preliminary Report on Patentability dated Nov. 5, 2020", 8 pgs.

"International Application Serial No. PCT/US2019/028997, International Search Report dated Aug. 22, 2019", 2 pgs.

"International Application Serial No. PCT/US2019/028997, Written Opinion dated Aug. 22, 2019", 6 pgs.

Allen-Bradley, "AC Braking Basics", Web article, Rockwell Automation, Rockwell International Corporation, [Online], Retrieved from the Internet: <http://literature.rockwellautomation.com/idc/groups/literature/documerits/wp/drives-wp004_-enp.pdf>, (Feb. 2001), 4 pgs.

Allen-Bradley, "What is Regeneration?, Braking / Regeneration Manual: Regeneration Overview", Revision 1.0. Rockwell Automation, [Online]. Retrieved from the Internet: <https://www.ab.com/supportlabdrives/documentation/techpapers/RegenOverview01.pdf> Accessed Apr. 24, 2017, 6 pgs.

* cited by examiner

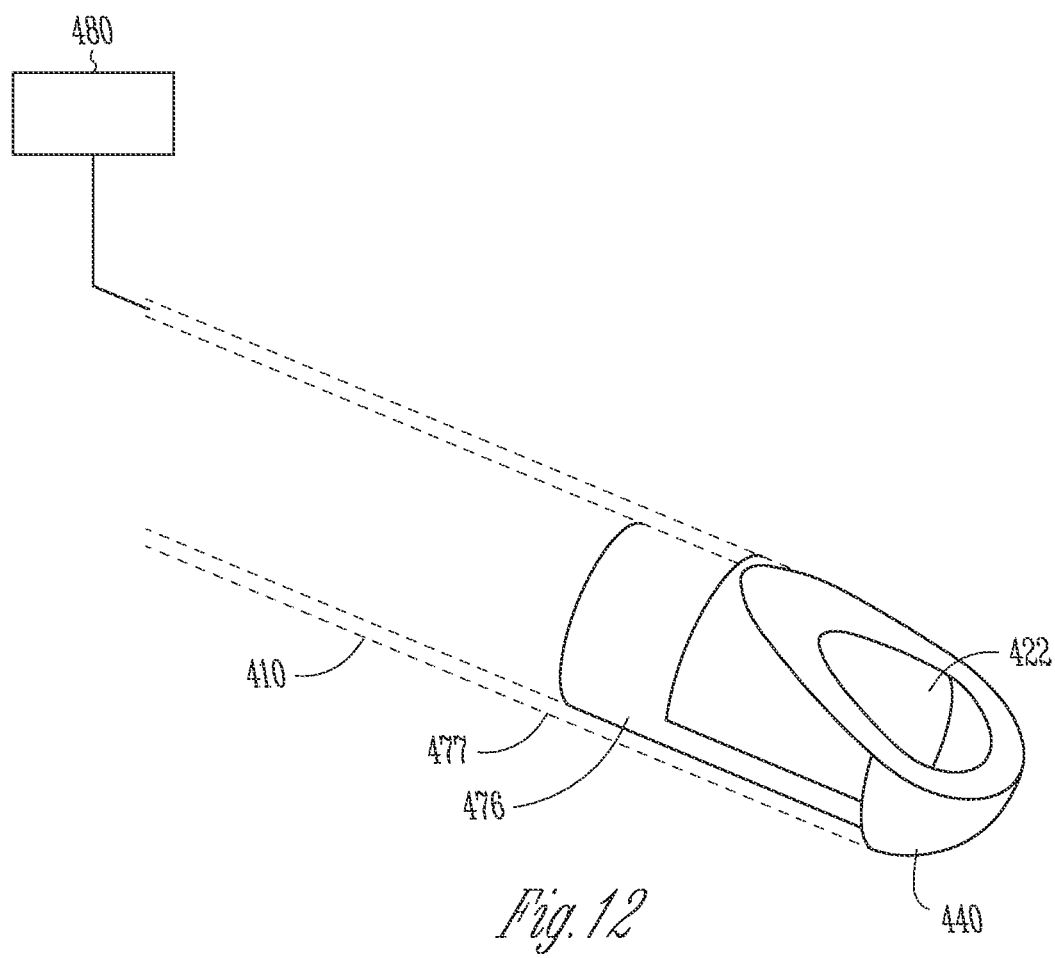

ARTHROSCOPIC DEVICES AND METHODS

CROSS-REFERENCE TO RELATED APPLICATION

The present application claims the benefit of provisional application No. 62/663,877, filed on Apr. 27, 2018, the full disclosure of which is incorporated herein by reference.

BACKGROUND OF THE INVENTION

1. Field of the Invention

This invention relates to a medical system that includes variations of motor-driven tubular cutter or arthroscopic shavers that are configured for both mechanical cutting and electrosurgical cutting, ablation and coagulation procedures.

In endoscopic and other surgical procedures including subacromial decompression, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

To promote efficiency, some endoscopic tool systems include reusable hand piece and a selection of interchangeable tool probes having different working ends. Such working ends may each have two or more functionalities, such as soft tissue removal and hard tissue resection, so such tools systems can provide dozens of specific functionalities, providing great flexibility. While providing significant flexibility, the large variety of surgical procedures and anatomical differences require a large number of specific tool functionalities.

It is therefore an object of the present invention to provide additional interchangeable and other tool probes and methods for their use, such as improved arthroscopic tissue cutting probes and removal system wherein a motor-driven electrosurgical device is provided for selectively cutting and removing bone or soft tissue from a joint or other site. It is a further object invention to a single arthroscopic cutting probe or other handheld device that is capable of both mechanical and electrosurgically enhanced cutting of both soft and hard tissues using a rotating burr cutter. At least some of these objectives will be met by the inventions described herein.

2. Description of the Background Art

Related, commonly owned patents and published applications include: U.S. Pat. Nos. 8,221,404; 8,323,280; 9,204,918; 9,277,954; 9,247,983; 9,592,085; 9,585,675; 9,603,656; 9,681,913; 9,855,675; 10,028,767; 10,052,149; 9,795,434; and 10,022,140; and U.S. Pat. Publication Nos. US 2016-0113706; US 2016-0157916; US 2017-0128083; US 2017-0172648; US 2017-0258519; US 2017-0258512; US 2017-0290602; US 2017-0303990; US 2017-0252099; US 2018-0000534; US 2018-0161088; US 2018-0008334; US 2018-0093391; US 2019-0015151; US 2018-0263649; US 2019-0083121; US 2019-0008538; US 2018-0303509; US 2018-0317957; US 2019-0021788; US 2019-0059983; and US 2019-0008541, the full disclosures of which are incorporated herein by reference.

SUMMARY OF THE INVENTION

The present invention provides improved apparatus methods for resecting tissue in arthroscopic and other surgical procedures. In particular, the present invention provides a single tool, typically in the form of an arthroscopic cutting probe, which can resect tissue using a rotating burr cutter both mechanically and with electrosurgical enhancement. The tool may employ a distal cutting member located at the distal end of a shaft assembly where at least a portion of an exterior surface of the distal cutting member is electrically insulated. One or more burr elements extend radially outwardly from the electrically insulated portion of the exterior surface of the distal cutting member where the burr element(s) are electrically conductive to form one or more active electrodes. The burrs are designed so that when the distal cutting member is rotated and engaged against tissue, the burrs will resect the tissue either mechanically or with electrosurgical enhancement when a radiofrequency (RF) current is applied to the electrically conductive burr elements.

This, in a first aspect, an arthroscopic cutting probe comprises a shaft assembly having a distal end, a proximal end, and a longitudinal axis. A distal cutting member is rotatably attached to the distal end of the shaft assembly, and at least a portion of an exterior surface of the distal cutting member is electrically insulated, typically the entire portion of the surface which is exposed to saline or other surgical environments in use. One or more burr elements extend radially outwardly from the electrically insulated portion of the exterior surface of the distal cutting member where the burr elements form active electrodes when the RF current is applied. Typically, the burr elements will be formed from a metal and will have exposed surfaces located above the electrically insulated surface of the cutting member.

In specific embodiments, the shaft member comprises an inner sleeve rotatably received in a longitudinal bore of an outer sleeve. The distal cutting member is typically attached to a distal end of the inner sleeve and often comprises a cylindrical metal core encased in a dielectric cover. In specific instances, the one or more burr elements extend radially outwardly from an outer surface of the metal core and through the dielectric cover.

In other instances, the distal cutting member may have one or more windows formed through the metal core and the dielectric cover to form a path from an exterior region surrounding the distal cutting member into an interior channel of the cylindrical metal core. The interior channel of the cylindrical metal core typically opens contiguously to a longitudinal passageway extending axially through the inner sleeve, and the inner sleeve is typically configured to be coupled to a negative pressure source to draw a partial vacuum through the longitudinal passageway, the interior channel, and the one or more windows formed through the metal core and the dielectric cover. In this way, the arthroscopic cutting probe can be operated to draw a vacuum against the tissue surface to be resected to enhance tissue engagement and resection and further to remove tissue debris generated by the tissue resection.

In many embodiments, the distal cutting member will have at least two burr elements located on opposing sides thereof, typically having from 2 to 10 burr elements on opposing sides thereof.

The dielectric cover may comprise any suitably material capable of withstanding the cutting operations, typically being a ceramic material, a polymer material, a glass, or combinations thereof. In some embodiments, the dielectric cover is formed by molding a polymeric or other material over the metal core, while in other instances the dielectric cover may be formed by coating a thin layer of dielectric material over the metal core, e.g. spray coating, dip coating, painting, or the like.

In still further specific instances, the cutting member may have a bullet shape with a generally hemispherically distal tip. In such instances, the hemispherical distal tip of the cutting member will usually extend distally through an open end of the outer sleeve in which the distal cutting member rotates.

In still further aspects of the present invention, the one or more burr elements of the arthroscopic cutting probes of the present invention may be adapted or configured for igniting a plasma when rotated at rotational speeds of 1,000 RPM or greater. In such instances, the one or more burr elements typically have the surface area adapted for igniting a plasma at rotational speeds ranging from 1000 RPM to 20,000 RPM. In still further instances, the one or more burr elements have a surface area adapted for igniting a plasma with an applied RF power of 400 W or less. More specifically, the burr elements may have a total electrically conductive surface area of less than 50 mm$^2$, often less than 25 mm$^2$, and in many instances less than 15 mm$^2$.

In certain aspects of the present invention, surgical cutting systems comprise an arthroscopic cutting probe as described above in combination with a motor drive unit, a RF power supply and a controller. The motor drive unit is configured to be coupled to the shaft assembly, typically to the inner and outer sleeves of the shaft assembly, to locate the cutting member to engage tissue for tissue resection. The RF power supply is usually configured to be coupled to the burr elements which act as active electrodes and to be connected to a separate return electrode structure. The return electrode structure may be formed on or as part of an exterior of the shaft assembly for bipolar operation or alternatively may be provided as a separate external pad for monopolar operation. The controllers typically configured to control the motor drive unit in the RF power supply.

In specific instances, the controller of the arthroscopic cutting systems is configured to operate the motor drive and the RF power supply in a first mode for mechanical tissue cutting where the motor drive is activated and the RF source is not activated. The controller may alternatively operate the motor drive and the RF power supply in a second mode for a combination of electrical and surgical tissue cutting where the RF power supply is activated in addition to the motor drive.

The RF cutting systems of the present invention will usually further comprise a negative pressure source configured to be coupled to the longitudinal passageway of the inner sleeve to draw tissue through the one or more windows formed in the distal cutting member, for example in order to help engage the distal cutting member against a surface of the target tissue to be resected and/or to draw tissue debris resulting from the resection into the cutting probe for extraction.

In the third aspect of the present invention, methods for resecting tissue comprise providing an arthroscopic cutting probe as in any of the embodiments described above. The burr elements of the distal cutting member of the probe are engaged against tissue to be resected, and the distal cutting member is rotated to engage the burr elements against the tissue and to resect the tissue, either by solely mechanical cutting or by electrosurgically enhanced cutting.

In certain methods of the present invention, the distal cutting member may be rotated during at least some time periods without RF current to the electrodes in a first mechanical resection mode of operation. In other time periods, the distal cutting member may be rotated concurrently to the burr elements which act as active electrodes in a second electrosurgical mode of operation. Usually in either the mechanical or the electrosurgically enhanced resection protocols, a negative pressure will be applied to a longitudinal passageway in the inner sleeve to draw tissue through the windows and the distal cutting member to either enhance engagement or extract cutting debris as described elsewhere. The cutting methods of the present invention are effective with both hard tissue and soft tissue, with the electrosurgical enhancement being of particular use when resecting hard tissue.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

FIG. 12 is perspective view of the dielectric housing of FIG. 11A.

DETAILED DESCRIPTION OF THE INVENTION

The present invention relates to bone cutting and tissue removal devices and related methods of use. Several variations of the invention will now be described to provide an overall understanding of the principles of the form, function and methods of use of the devices disclosed herein. In general, the present disclosure provides for variations of arthroscopic tools adapted for cutting bone, soft tissue, meniscal tissue, and for RF ablation and coagulation. The arthroscopic tools are typically disposable and are configured for detachable coupling to a non-disposable hand piece that carries a motor drive component. This description of the general principles of this invention is not meant to limit the inventive concepts in the appended claims.

Figure 1:
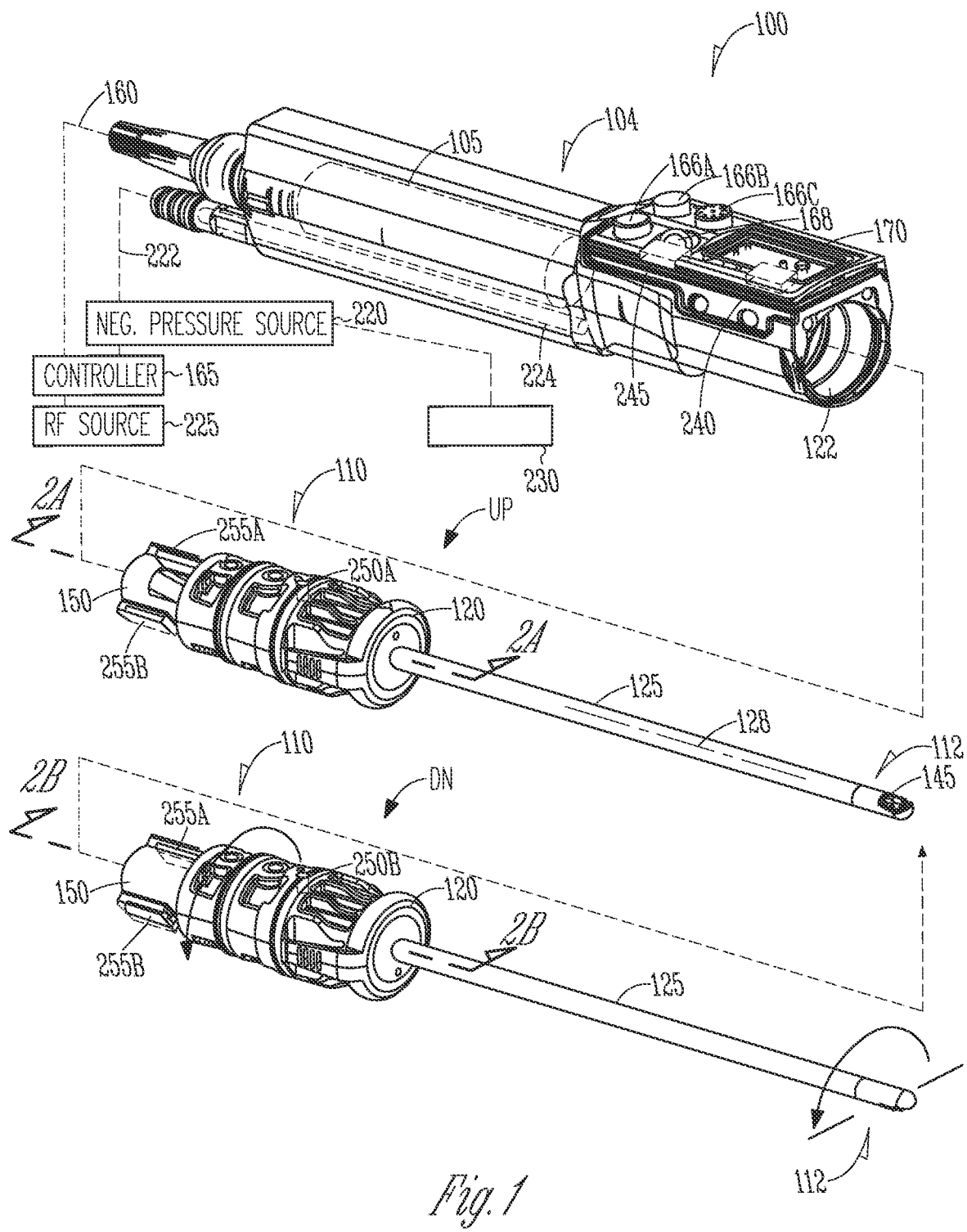
FIG. 1 is a perspective view of an arthroscopic cutting system that includes reusable hand piece with a motor drive and a detachable single-use cutting probe, wherein the cutting probe is shown in two orientations as it may be coupled to the hand piece with the probe and working end in upward orientation or a downward orientation relative to the hand piece, and wherein the hand piece includes an LCD screen for displaying operating parameters of system during use together with control actuators on the hand piece.

In one variation shown in FIG. 1, the arthroscopic system 100 of the present invention provides a hand piece 104 with motor drive 105 and a disposable shaver assembly or probe 110 with a proximal hub 120 that can be received by receiver or bore 122 in the hand piece 104. In one aspect, the probe 110 has a working end 112 that carries a high-speed rotating cutter that is configured for use in many arthroscopic surgical applications, including but not limited to treating bone in shoulders, knees, hips, wrists, ankles and the spine.

Figure 2A:
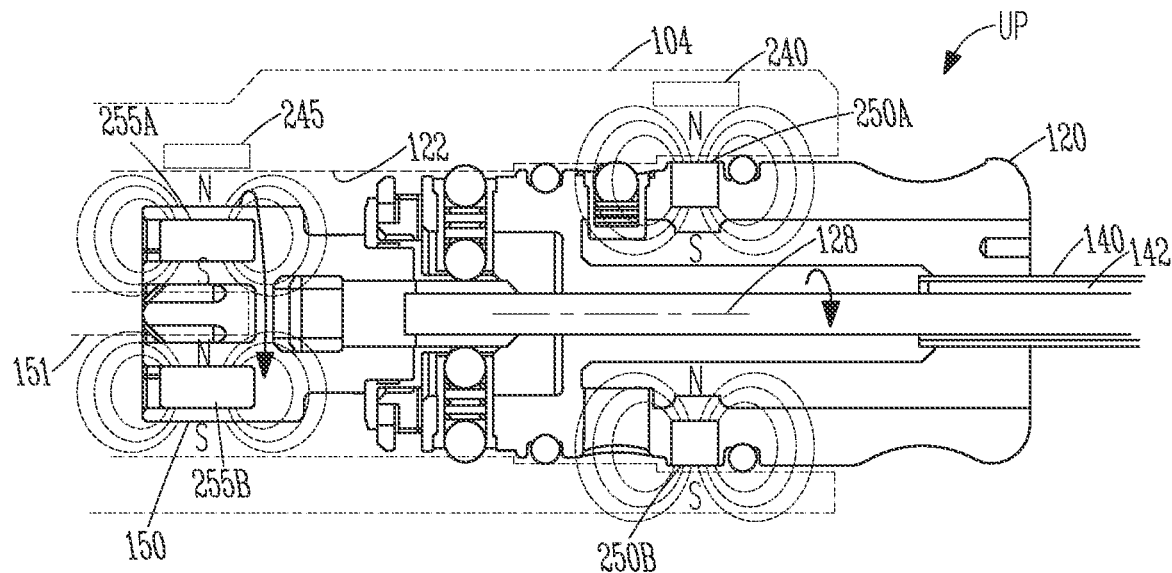
FIG. 2A is an enlarged longitudinal sectional view of the hub of the probe of FIG. 1 taken along line 2A-2A of FIG. 1 with the hub and probe in an upward orientation relative to the hand piece, further showing Hall effect sensors carried by the hand piece and a plurality of magnets carried by the probe hub for device identification, for probe orientation and determining the position of motor driven components of the probe relative to the hand piece.
Figure 3A:
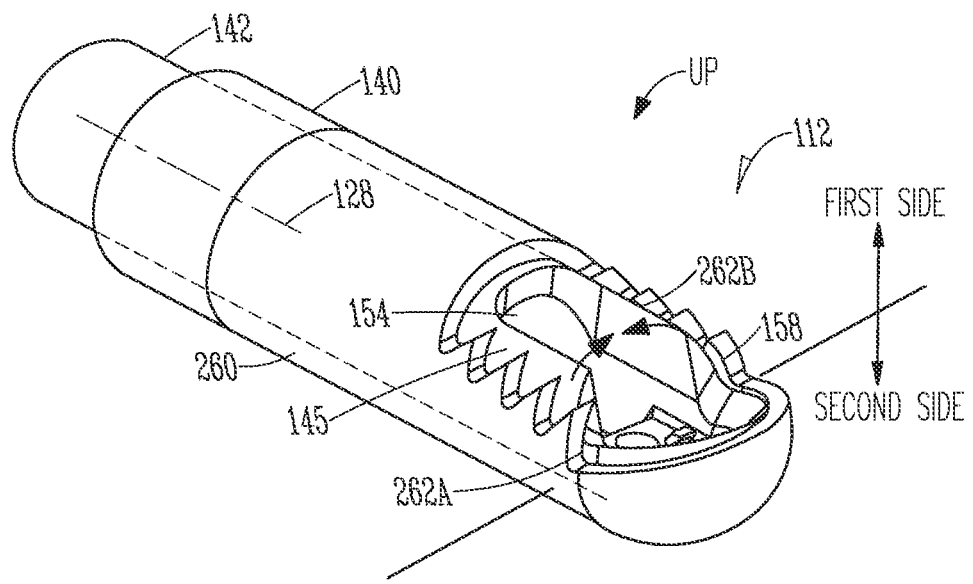
FIG. 3A is an enlarged perspective view of the working end of the probe of FIG. 1 in an upward orientation with the rotatable cutting member in a first position relative to the outer sleeve wherein the window in the cutting member is aligned with the window of the outer sleeve.
Figure 3B:
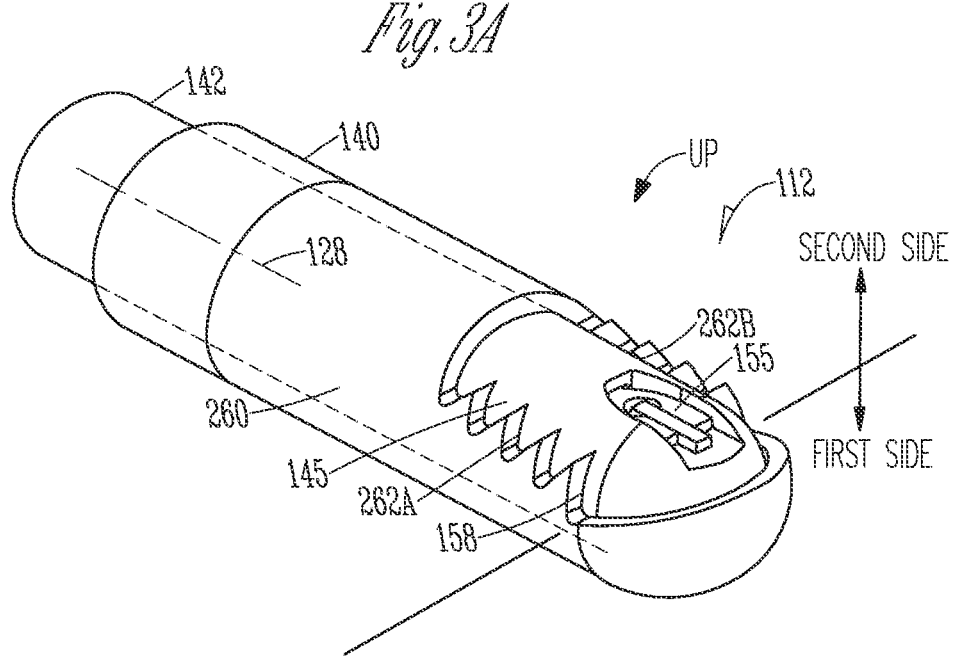
FIG. 3B is a perspective view of the working end of FIG. 1 in an upward orientation with the rotatable cutting member in a second position relative to the outer sleeve wherein the electrode carried by the cutting member is aligned with a centerline of the window of the outer sleeve.

In FIGS. 1, 2A and 3A, it can be seen that probe 110 has a shaft 125 extending along longitudinal axis 128 that comprises an outer sleeve 140 and an inner sleeve 142 rotatably disposed therein with the inner sleeve 142 carrying a distal ceramic cutting member 145 (FIG. 3A). The shaft 125 extends from the proximal hub 120 wherein the outer sleeve 140 is coupled in a fixed manner to the hub 120 which can be an injection molded plastic, for example, with the outer sleeve 140 insert molded therein. The inner sleeve 142 is coupled drive coupling 150 that is configured for coupling to the rotating motor shaft 151 of motor drive unit 105. More in particular, the rotatable cutting member 145 that is fabricated of a ceramic material with sharp cutting edges on opposing sides 152a and 152b of window 154 therein for cutting soft tissue. The motor drive 105 is operatively coupled to the ceramic cutter to rotate the cutting member at speeds ranging from 1,000 rpm to 20,000 rpm. In FIG. 3B, it can be seen that cutting member 145 also carries an RF electrode 155 in a surface opposing the window 154. The cutting member 145 rotates and shears tissue in the toothed opening or window 158 in the outer sleeve 140 (FIG. 3A). A probe of the type shown in FIG. 1 is described in more detail in co-pending and commonly owned patent application Ser. No. 15/421,264 filed Jan. 31, 2017 titled ARTHROSCOPIC DEVICES AND METHODS which is incorporated herein in its entirety by this reference.

As can be seen in FIG. 1, the probe 110 is shown in two orientations for detachable coupling to the hand piece 104. More particularly, the hub 120 can be coupled to the hand piece 104 in an upward orientation indicated at UP and a downward orientation indicated at DN where the orientations are 180° opposed from one another. It can be understood that the upward and downward orientations are necessary to orient the working end 112 either upward or downward relative to the hand piece 104 to allow the physician to interface the cutting member 145 with targeted tissue in all directions without having to manipulate the hand piece in 360° to access tissue.

In FIG. 1, it can be seen that the handle 104 is operatively coupled by electrical cable 160 to a controller 165 which controls the motor drive unit 105. Actuator buttons 166a, 166b or 166c on the handle 104 can be used to select operating modes, such as various rotational modes for the ceramic cutting member 145. In one variation, a joystick 168 can be moved forward and backward to adjust the rotational speed of the ceramic cutting member 145. The rotational speed of the cutter can continuously adjustable, or can be adjusted in increments up to 20,000 rpm. An LCD screen 170 is provided in the hand piece for displaying operating parameters, such as cutting member RPM, mode of operation, etc.

Figure 4:
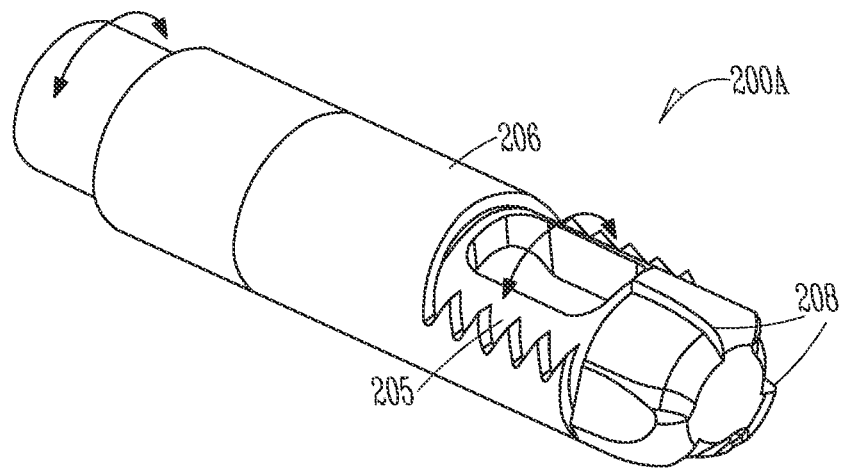
FIG. 4 is a perspective view of a working end of a variation of a probe that may be detachably coupled to the hand piece of FIG. 1, wherein the working end includes a bone burr extending distally from the outer sleeve.
Figure 5:
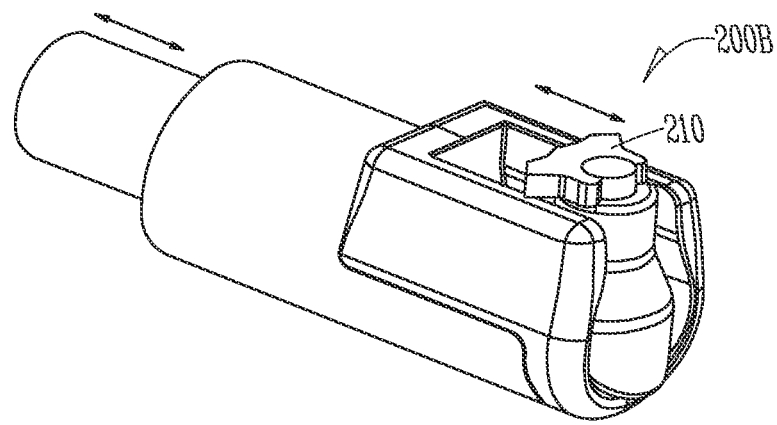
FIG. 5 is a perspective view of a working end of a variation of a probe that may be detachably coupled to the hand piece of FIG. 1, wherein the working end has a reciprocating electrode.
Figure 6:
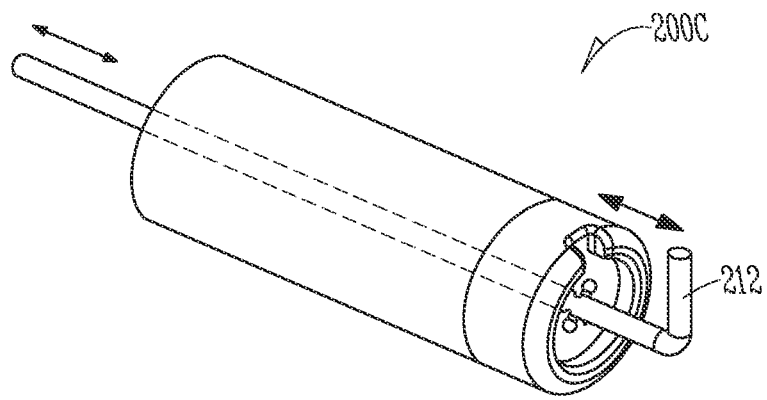
FIG. 6 is a perspective view of a working end of another variation of a probe that may be detachably coupled to the hand piece of FIG. 1, wherein the working end has a hook electrode that has extended and non-extended positions.
Figure 7:
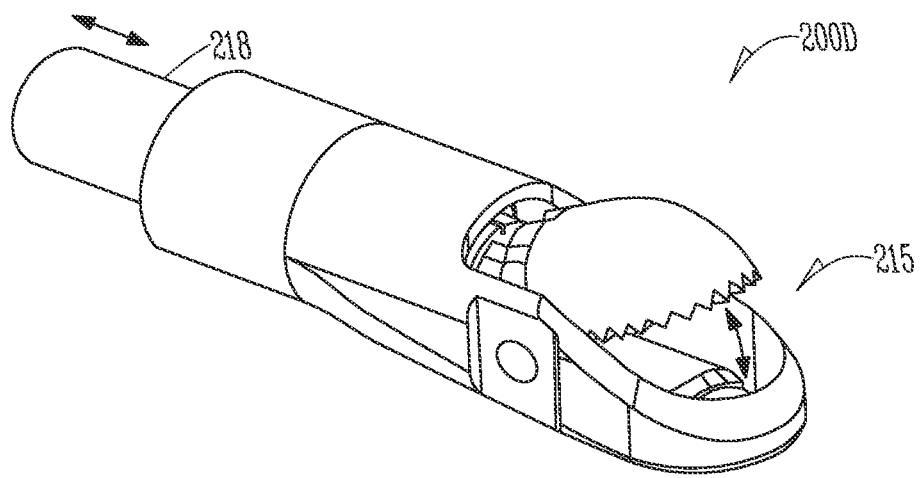
FIG. 7 is a perspective view of a working end of yet another variation of a probe that may be detachably coupled to the hand piece of FIG. 1, wherein the working end has an openable-closeable jaw structure for cutting tissue.

It can be understood from FIG. 1 that the system 100 and hand piece 104 is adapted for use with various disposable probes which can be designed for various different functions and procedures For example, FIG. 4 illustrates a different variation of a probe working end 200A that is similar to working end 112 of probe 110 of FIGS. 3A-3B, except the ceramic cutting member 205 extends distally from the outer sleeve 206 and the cutting member has burr edges 208 for cutting bone. The probe of FIG. 4 is described in more detail in co-pending and commonly owned patent application Ser. No. 15/271,184 filed Sep. 20, 2016 titled ARTHROSCOPIC DEVICES AND METHODS. FIG. 5 illustrates a different variation of a probe working end 200B with a reciprocating electrode 210 in a type of probe described in more detail in co-pending and commonly owned patent application Ser. No. 15/410,723 filed Jan. 19, 2017 titled ARTHROSCOPIC DEVICES AND METHODS. In another example, FIG. 6 illustrates another variation of a probe working end 200C that has an extendable-retractable hook electrode 212 in a probe type described in more detail in co-pending and commonly owned patent application Ser. No. 15/454,342 filed Mar. 9, 2017 titled ARTHROSCOPIC DEVICES AND METHODS. In yet another example, FIG. 7 illustrates a variation of a working end 200D in a probe type having an openable-closable jaw structure 215 actuated by reciprocating member 218 for trimming meniscal tissue or other tissue as described in more detail in co-pending and commonly owned patent application Ser. No. 15/483,940 filed Apr. 10, 2017 titled ARTHROSCOPIC DEVICES AND METHODS. All of the probes of FIGS. 4-7 can have a hub similar to hub 120 of probe 110 of FIG. 1 for coupling to the same hand piece 104 of FIG. 1, with some of the probes (see FIGS. 5-7) having a hub mechanism for converting rotational motion to linear motion. All of the patent applications just identified in this paragraph are incorporated herein by this reference.

FIG. 1 further shows that the system 100 also includes a negative pressure source 220 coupled to aspiration tubing 222 which communicates with a flow channel 224 in hand piece 104 and can cooperate with any of the probes 110, 200A, 200B or 200C of FIGS. 1-3B, 4, 5 and 6. In FIG. 1 it also can be seen that the system 100 includes an RF source 225 which can be connected to an electrode arrangement in any of the probes 110, 200A, 200B or 200C of FIGS. 1-3B, 4, 5 and 6. The controller 165 and microprocessor therein together with control algorithms are provided to operate and control all functionality, which includes controlling the motor drive 105 to move a motor-driven component of any probe working end 110, 200A, 200B or 200C, as well as for controlling the RF source 225 and the negative pressure source 220 which can aspirate fluid and tissue debris to collection reservoir 230.

As can be understood from the above description of the system 100 and hand piece 104, the controller 165 and controller algorithms need to be configured to perform and automate many tasks to provide for system functionality. In a first aspect, controller algorithms are needed for device identification so that when any of the different probes types 110, 200A, 200B, 200C or 200D of FIGS. 1 and 4-7 are coupled to hand piece 104, the controller 165 will recognize the probe type and then select algorithms for operating the motor drive 105, RF source 225 and negative pressure source 220 as is needed for the particular probe. In a second aspect, the controller is configured with algorithms that identify whether the probe is coupled to the hand piece 104 in an upward or downward orientation relative to the hand piece, wherein each orientation requires a different subset of the operating algorithms. In another aspect, the controller has separate control algorithms for each probe type wherein some probes have a rotatable cutter while others have a reciprocating electrode or jaw structure. In another aspect, most if not all the probes 110, 200A, 200B, 200C and 200D (FIGS. 1, 4-7) require a default "stop" position in which the motor-driven component is stopped in a particular orientation within the working end. For example, a rotatable cutter 145 with an electrode 155 needs to have the electrode centered within an outer sleeve window 158 in a default position such as depicted in FIG. 3B. Some of these systems, algorithms and methods of use are described next.

Figure 2B:
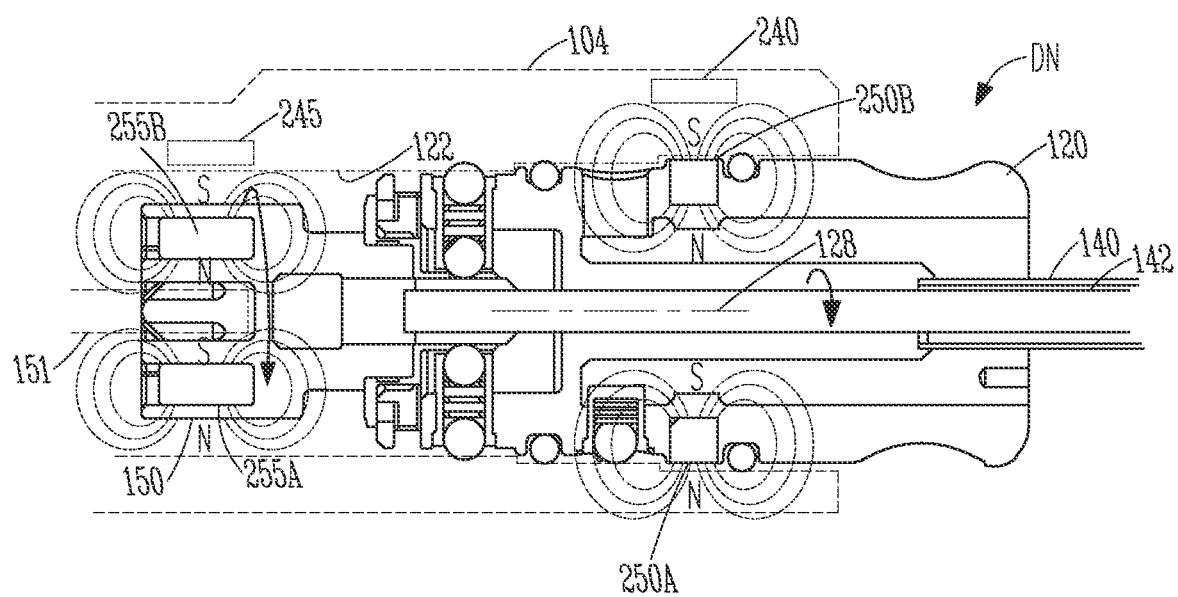
FIG. 2B is a sectional view of the hub of FIG. 1 taken along line 2B-2B of FIG. 1 with the hub and probe in a downward orientation relative to the hand piece showing the Hall effect sensor and magnets having a different orientation compared to that of FIG. 2A.

Referring to FIGS. 1 and 2A-2B, it can be seen that hand piece 104 carries a first Hall effect sensor 240 in a distal region of the hand piece 104 adjacent the receiving passageway 122 that receives the hub 120 of probe 110. FIG. 2A corresponds to the probe 110 and working end 112 in FIG. 1 being in the upward orientation indicated at UP. FIG. 2B corresponds to probe 110 and working end 112 in FIG. 1 being in the downward orientation indicated at DN. The hand piece 104 carries a second Hall effect sensor 245 adjacent the rotatable drive coupling 150 of the probe 110. The probe 110 carries a plurality of magnets as will be described below that interact with the Hall effect sensors 240, 245 to provide multiple control functions in cooperation with controller algorithms, including (i) identification of the type of probe coupled to the hand piece, (ii) the upward or downward orientation of the probe hub 120 relative to the hand piece 104, and (iii) the rotational position and speed of rotating drive collar 150 from which a position of either rotating or reciprocating motor-driven components can be determined.

The sectional views of FIGS. 2A-2B show that hub 120 of probe 110 carries first and second magnets 250a and 250b in a surface portion thereof. The Hall sensor 240 in hand piece 104 is in axial alignment with either magnet 250a or 250b when the probe hub 120 is coupled to hand piece 104 in an upward orientation (FIGS. 1 and 2A) or a downward orientation (FIGS. 1 and 2B). In one aspect as outlined above, the combination of the magnets 250a and 250b and the Hall sensor 240 can be used to identify the probe type. For example, a product portfolio may have from 2 to 10 or more types of probes, such as depicted in FIGS. 1 and 4-7, and each such probe type can carry magnets 250a, 250b having a specific, different magnetic field strength. Then, the Hall sensor 240 and controller algorithms can be adapted to read the magnetic field strength of the particular magnet(s) in the probe which can be compared to a library of field strengths that correspond to particular probe types. Then, a Hall identification signal can be generated or otherwise provided to the controller 165 to select the controller algorithms for operating the identified probe, which can include parameters for operating the motor drive 105, negative pressure source 220 and/or RF source 225 as may be required for the probe type. As can be seen in FIGS. 1, 2A and 2B, the probe hub 120 can be coupled to hand piece 104 in upward and downward orientations, in which the North (N) and South (S) poles of the magnets 250a, 250b are reversed relative to the probe axis 128. Therefore, the Hall sensor 240 and associated algorithms look for magnetic field strength regardless of polarity to identify the probe type.

Referring now to FIGS. 1, 2A-2B and 3A-3B, the first and second magnets 250a and 250b with their different orientations of North (N) and South (S) poles relative to central longitudinal axis 128 of hub 120 are also used to identify the upward orientation UP or the downward orientation DN of hub 120 and working end 112. In use, as described above, the physician may couple the probe 110 to the hand piece receiving passageway 122 with the working end 112 facing upward or downward based on his or her preference and the targeted tissue. It can be understood that controller algorithms adapted to stop rotation of the cutting member 145 in the window 158 of the outer sleeve 104 of working end 112 need to "learn" whether the working end is facing upward or downward, because the orientation or the rotating cutting member 145 relative to the handpiece and Hall sensor 240 would vary by 180°. The Hall sensor 240 together with a controller algorithm can determine the orientation UP or the downward orientation DN by sensing whether the North (N) or South (S) pole of either magnet 250a or 250b is facing upwardly and is proximate the Hall sensor 240.

In another aspect of the invention, in probe 110 (FIG. 1) and other probes, the motor-driven component of a working end, such as rotating cutter 145 of working end 112 of FIGS. 1 and 3A-3B needs to stopped in a selected rotational position relative to a cut-out opening or window 158 in the outer sleeve 140. Other probe types may have a reciprocating member or a jaw structure as described above, which also needs a controller algorithm to stop movement of a moving component in a selected position, such as the axial-moving electrodes of FIGS. 5-6 and the jaw structure of FIG. 7. In all probes, the motor drive 105 couples to the rotating drive coupling 150, thus sensing the rotational position of the drive coupling 150 can be used to determine the orientation of the motor-driven component in the working end. More in particular, referring to FIGS. 1 and 2A-2B, the drive coupling 150 carries third and fourth magnets 255a or 255b with the North (N) and South (S) poles of magnets 255a or 255b being reversed relative to the probe axis 128. Thus, Hall sensor 245 can sense when each magnet rotates passes the Hall sensor and thereby determine the exact rotational position of the drive coupling 150 twice on each rotation thereof (once for each magnet 255a, 255b). Thereafter, a controller tachometer algorithm using a clock can determine and optionally display the RPM of the drive coupling 150 and, for example, the cutting member 145 of FIG. 3A.

In another aspect of the invention, the Hall sensor 245 and magnets 255a and 255b (FIGS. 1 and 2A) are used in a set of controller algorithms to stop the rotation of a motor-driven component of a working end, for example, cutting member 145 of FIGS. 1 and 3A-3B in a pre-selected rotational position. In FIG. 3A, it can be seen that the inner sleeve 142 and a "first side" of cutting member 145 and window 154 therein is stopped and positioned in the center of window 158 of outer sleeve 140. The stationary position of cutting member 145 and window 154 in FIG. 3A may be used for irrigation or flushing of a working space to allow for maximum fluid outflow through the probe.

FIG. 3B depicts inner sleeve 142 and a "second side" of cutting member 145 positioned about the centerline of window 158 in the outer sleeve 140. The stationary or stopped position of cutting member 145 in FIG. 3B is needed for using the RF electrode 155 to ablate or coagulate tissue. It is important that the electrode 155 is maintained along the centerline of the outer sleeve window 158 since the outer sleeve 140 typically comprises return electrode 260. The position of electrode 155 in FIG. 3B is termed herein a "centerline default position". If the cutting member 145 and electrode 155 were rotated so as to be close to an edge 262a or 262b of window 158 in outer sleeve 140, RF current could arc between the electrodes 155 and 260 and potentially cause a short circuit disabling the probe. Therefore, a robust and reliable stop mechanism is required which is described next.

As can be understood from FIGS. 1 and 2A-2B, the controller 165 can always determine in real time the rotational position of drive coupling 150 and therefore the angular or rotational position of the ceramic cutting member 145 and electrode 155 can be determined. A controller algorithm can further calculate the rotational angle of the electrode 155 away from the centerline default position as the Hall sensor 245 can sense lessening of magnetic field strength as a magnet 255a or 255b in the drive coupling 150 rotates the electrode 155 away from the centerline default position. Each magnet has a specified, known strength and the algorithm can use a look-up table with that lists fields strengths corresponding to degrees of rotation away from the default position. Thus, if the Hall signal responsive to the rotated position of magnet 255a or 255b drops a specified amount from a known peak value in the centerline default position, it means the electrode 155 has moved away from the center of the window 158. In one variation, if the electrode 155 moves a selected rotational angle away from the centerline position during RF energy delivery to the electrode, the algorithm turns off RF current instantly and alerts the physician by an aural and/or visual signal, such as an alert on the LCD screen 170 on hand piece 104 and/or on a screen on a controller console (not shown). The termination of RF current delivery thus prevents the potential of an electrical arc between electrode 155 and the outer sleeve electrode 260.

It can be understood that during use, when the electrode 155 is in the position shown in FIG. 3B, the physician may be moving the energized electrode over tissue to ablate or coagulate tissue. During such use, the cutting member 145 and electrode 155 can engage or catch on tissue which inadvertently rotate the electrode 155 out of the default centerline position. Therefore, the system provides a controller algorithm, herein called an "active electrode monitoring" algorithm, wherein the controller continuously monitors position signals generated by Hall sensor 245 during RF energy delivery in both an ablation mode and a coagulation mode to determine if the electrode 155 and inner sleeve 142 have been bumped off the centerline position. In a variation, the controller algorithms can be configured to then re-activate the motor drive 105 to move the inner sleeve 142 and electrode 155 back to the default centerline position sleeve if electrode 155 had been bumped off the centerline position. In another variation, the controller algorithms can be configured to again automatically deliver RF current to RF electrode 155 when it is moved back to the to the default centerline position. Alternatively, the controller 165 can require the physician to manually re-start the delivery of RF current to the RF electrode 155 when it is moved back to the to the centerline position. In an aspect of the invention, the drive coupling 150 and thus magnets 255a and 255b are attached to inner sleeve 142 and cutting member 145 in a pre-determined angular relationship relative to longitudinal axis 128 so that the Hall sensor generates signals responsive to magnets 255a, 255b is the same for all probes within a probe type to thus allow the controller algorithm to function properly.

Figure 8:
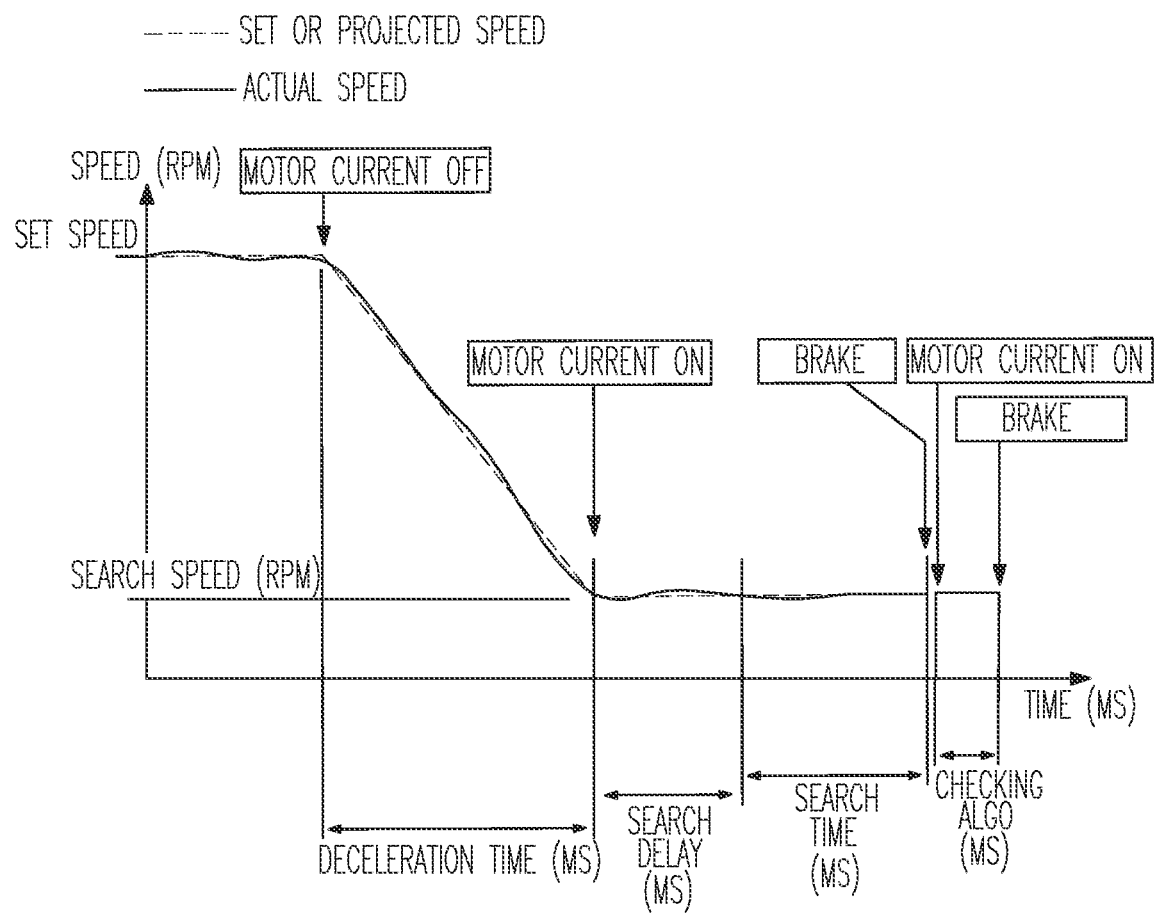
FIG. 8 is a chart relating to set speeds for a probe with a rotating cutting member as in FIGS. 1 and 3A that schematically shows the method used by a controller algorithm for stopping rotation of the cutting member in a selected default position.

Now turning to the stop mechanism or algorithms for stopping movement of a motor-driven component of working end 112, FIG. 8 schematically illustrates the algorithm and steps of the stop mechanism. In one variation, referring to FIG. 8, the stop mechanism corresponding to the invention uses (i) a dynamic braking method and algorithm to stop the rotation of the inner sleeve 142 and cutting member 145 (FIGS. 1, 3A-3B) in an initial position, and thereafter (ii) a secondary checking algorithm is used to check the initial stop position that was attained with the dynamic braking algorithm, and if necessary, the stop algorithm can re-activate the motor drive 105 to slightly reverse (or move forward) the rotation of drive coupling 150 and inner sleeve 142 as needed to position the cutting member 145 and electrode 155 within at the centerline position or within 0° to 5° of the targeted centerline default position. Dynamic braking is described further below. FIG. 8 schematically illustrates various aspects of controller algorithms for controlling the rotational speed of the cutting member and for stopping the cutting member 145 in the default centerline position.

In FIG. 8, it can be understood that the controller 165 is operating the probe 110 of FIGS. 1 and 3A-3B at a "set speed" which may be a PID controlled, continuous rotation mode in one direction or may be an oscillating mode where the motor drive 105 rotates the cutting member 145 in one direction and then reverses rotation as is known in the art. At higher rotational speeds such as 1,000 RPM to 20,000 RPM, it is not practical or feasible to acquire a signal from Hall sensor 245 that indicates the position of a magnet 255a or 255b in the drive coupling 150 to apply a stop algorithm. In FIG. 8, when the physician stop cutting with probe 110 by releasing actuation of an actuator button or foot pedal, current to the motor drive 105 is turned off. Thereafter, the controller algorithm uses the Hall sensor 245 to monitor deceleration of rotation of the drive coupling 150 and inner sleeve 142 until a slower RPM is reached. The deceleration period may be from 10 ms to 1 sec and typically is about 100 ms. When a suitable slower RPM is reached which is called a "search speed" herein (see FIG. 8), the controller 165 re-activates the motor drive 105 to rotate the drive coupling at a low speed ranging from 10 RPM to 1,000 RPM and in one variation is between 50 RPM and 250 RPM. An initial "search delay" period ranging from 50 ms to 500 ms is provided to allow the PID controller to stabilize the RPM at the selected search speed. Thereafter, the controller algorithm monitors the Hall position signal of magnet strength and when the magnet parameter reaches a predetermined threshold, for example, when the rotational position of drive coupling 150 and electrode 155 correspond to the centerline default position of FIG. 3B, the control algorithm then applies dynamic braking to instantly stop rotation of the motor drive shaft 151, drive coupling 150 and the motor-driven component of the probe. FIG. 8 further illustrates that the controller can check the magnet/drive coupling 150 position after the braking and stopping steps. If the Hall position signal indicates that the motor-driven component is out of the targeted default position, the motor drive 105 can be re-activated to move the motor-driven component and thereafter the brake can be applied again as described above.

Dynamic braking as shown schematically in FIG. 8 may typically stop the rotation of the drive coupling 150 with a variance of up to about 0°-15° of the targeted stop position, but this can vary even further when different types of tissue are being cut and impeding rotation of the cutting member 145, and also depending on whether the physician has completely disengaged the cutting member from the tissue interface when the motor drive is de-activated. Therefore, dynamic braking alone may not assure that the default or stop position is within a desired variance.

As background, the concept of dynamic braking is described in the following literature: https://www.ab.com/support/abdrives/documentation/techpapers/RegenOverview01.pdf and http://literature.rockwellautomation.com/idc/groups/literature/documents/wp/drives-wp004_-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called dynamic braking with the chopper transistor and related control and components called the chopper module and the power resistor called the dynamic brake resistor. The entire assembly of chopper module with dynamic brake resistor is sometimes referred to as the dynamic brake module. The dynamic brake resistor allows any magnetic energy stored in the parasitic inductance of that circuit to be safely dissipated during the turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, there is no longer any braking power left.

In another aspect of the invention, a method has been developed to increase the accuracy of the stopping mechanism which is a component of the positioning algorithm described above. It has been found that each magnet in a single-use probe may vary slightly from its specified strength. As described above, the positioning algorithm uses the Hall effect sensor 245 to continuously monitor the field strength of magnets 255a and 255b as the drive coupling 150 rotates and the algorithm determines the rotational position of the magnets and drive coupling based on the field strength, with the field strength rising and falling as a magnet rotates past the Hall sensor. Thus, it is important for the algorithm to have a field strength library that accurately corresponds to the degree of rotation away from a peak Hall signal when a magnet is adjacent the sensor 245. For this reason, an initial step of the positioning algorithm includes a "learning" step that allow the controller to learn the actual field strength of the magnets 255a and 255b which may vary from the specified strength. After a new single-use probe 110 (FIG. 1) is coupled to the hand piece 104, and after actuation of the motor drive 105, the positioning algorithm will rotate the drive coupling at least 180° and more often at least 360° while the Hall sensor 245 quantifies the field strength of the particular probe's magnets 255a and 255b. The positioning algorithm then stores the maximum and minimum Hall signals (corresponding to North and South poles) and calibrates the library of field strengths that correspond to various degrees of rotation away from a Hall min-max signal position when a magnet is adjacent the Hall sensor.

In general, a method of use relating to the learning algorithm comprises providing a hand piece with a motor drive, a controller, and a probe with a proximal hub configured for detachable coupling to the hand piece, wherein the motor drive is configured to couple to a rotating drive coupling in the hub and wherein the drive coupling carries first and second magnets with North and South poles positioned differently relative to said axis, and coupling the hub to the hand piece, activating the motor drive to thereby rotate the drive coupling and magnets at least 180°, using a hand piece sensor to sense the strength of each magnet, and using the sensed strength of the magnets for calibration in a positioning algorithm that is responsive to the sensor sensing the varying strength of the magnets in the rotating drive coupling to thereby increase accuracy in calculating the rotational position of the drive coupling 150.

Another aspect of the invention relates to an enhanced method of use using a probe working end with an electrode, such as the working end 112 of FIGS. 1 and 3B. As described above, a positioning algorithm is used to stop rotation of the electrode 155 in the default centerline position of FIG. 3B. An additional "slight oscillation" algorithm is used to activate the motor drive 105 contemporaneous with RF current to the electrode 155, particularly an RF cutting waveform for tissues ablation. The slight oscillation thus provides for a form of oscillating RF ablation. The slight oscillation algorithm rotates the electrode 155 in one direction to a predetermined degree of rotation, which the controller algorithms determine from the Hall position signals. Then, the algorithm reverses direction of the motor drive to rotate in the opposite direction until Hall position signals indicate that the predetermined degree of rotation was achieved in the opposite direction away from the electrode's default centerline position. The predetermined degree of angular motion can be any suitable rotation that is suitable for dimensions of the outer sleeve window, and in one variation is from 1° to 30° in each direction away from the centerline default position. More often, the predetermined degree of angular motion is from 5° to 15° in each direction away from the centerline default. The slight oscillation algorithm can use any suitable PID controlled motor shaft speed, and in one variation the motor shaft speed is from 50 RPM to 5,000 RPM, and more often from 100 RPM to 1,000 RPM. Stated another way, the frequency of oscillation can be from 20 Hz to 2,000 Hz and typically between 40 Hz and 400 Hz.

While the above description of the slight oscillation algorithm is provided with reference to electrode 155 on a rotating cutting member 145 of FIG. 3B, it should be appreciated that a reciprocating electrode 212 as shown in the working end 200C of FIG. 6 end could also be actuated with slight oscillation. In other words, the hook shape electrode 212 of FIG. 6 could be provided with a frequency of oscillation ranging from 20 Hz to 2,000 Hz and typically between 40 Hz and 400 Hz.

Figure 9A:
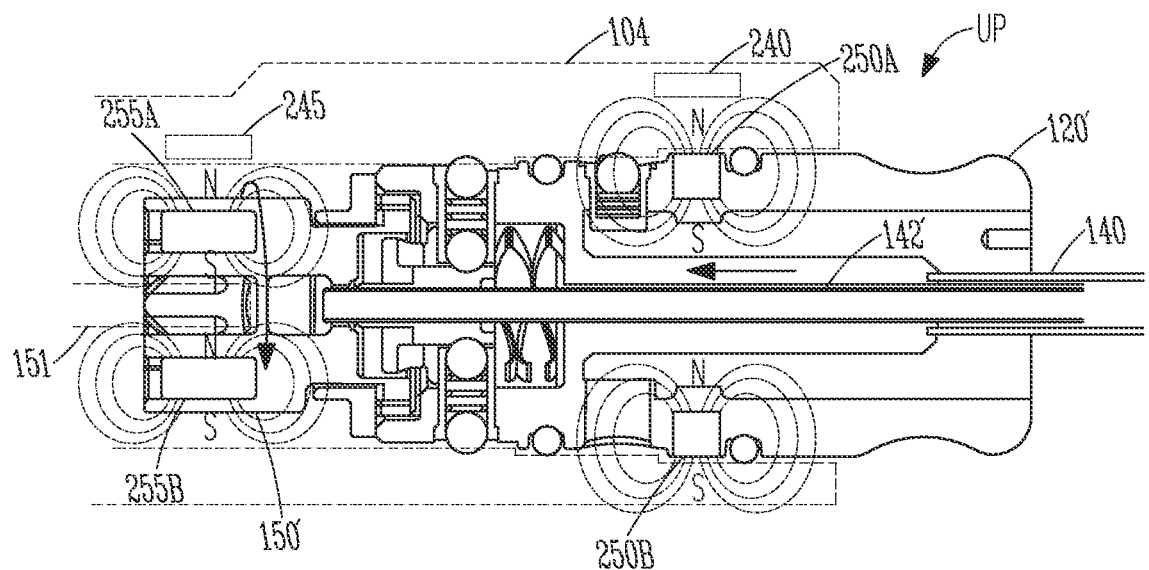
FIG. 9A is a longitudinal sectional view of a probe hub that is similar to that of FIG. 2A, except the hub of FIG. 9A has an internal cam mechanism for converting rotational motion to linear motion to axially reciprocate an electrode as in the working end of FIG. 5, wherein FIG. 9A illustrated the magnets in the hub and drive coupling are the same as in FIG. 2A and the hub is in an upward facing position relative to the hand piece.
Figure 9B:
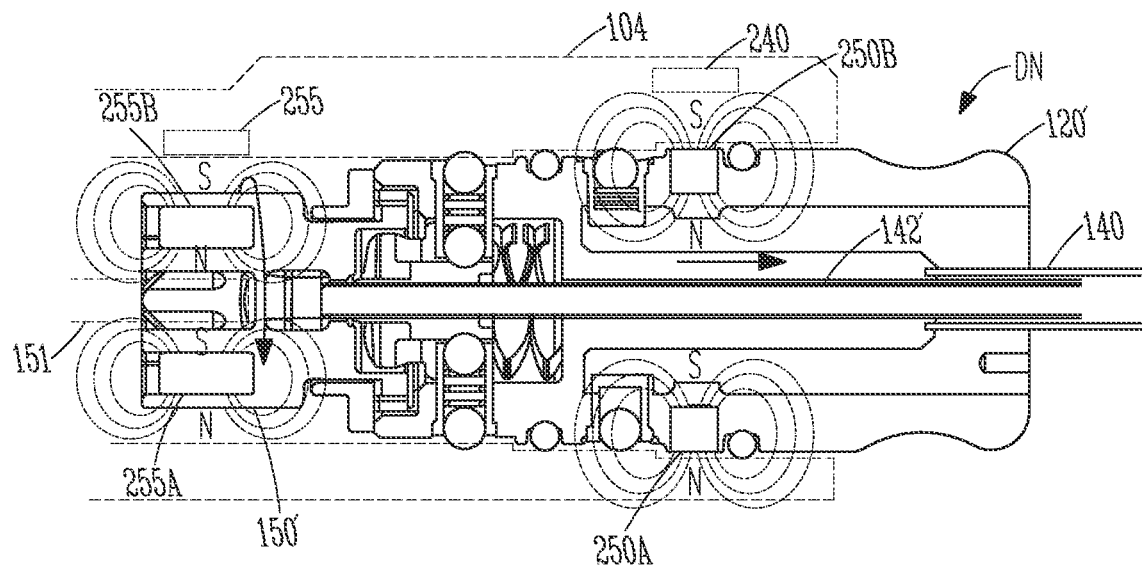
FIG. 9B is a sectional view of the hub of FIG. 9A rotated 180° in a downward facing position relative to the hand piece.

FIGS. 9A-9B are longitudinal sectional views of a probe hub 120' that corresponds to the working end 200B of FIG. 5 which has a reciprocating electrode 210. In FIGS. 9A-9B, the hand piece 104 and Hall affect sensors 240 and 245 are of course the same as described above as there is no change in the hand piece 104 for different types of probes. The probe hub 120' of FIGS. 9A-9B is very similar to the hub 120 of FIGS. 2A-2B with the first and second identification/orientation magnets 250a and 250b being the same. The third and fourth rotation al position magnets 255a and 255b also are the same and are carried by drive coupling 150'. The probe hub 120' of FIGS. 9A-9B only differs in that the drive coupling 150 rotates with a cam mechanism operatively coupled to inner sleeve 142' to convert rotational motion to linear motion to reciprocate the electrode 210 in working end 200B of FIG. 5. A similar hub for converting rotational motion to linear motion is provided for the working ends 200C and 200D of FIGS. 6 and 7, respectively, which each have a reciprocating component (212, 218) in its working end.

Now turning to FIGS. 10 and 11A-11C, another variation of an arthroscopic shaver or resection probe 400 is shown in which somewhat similar to that of FIGS. 1 and 3A-3B which comprises a tubular cutter having a proximal hub 402 coupled to an elongated shaft assembly 405. The shaft assembly comprises an outer sleeve 410 and a concentric inner sleeve 415 that extends along axis 418 to a working end 420. The hub 402 again is adapted for coupling to a hand piece and motor drive operated by a controller and controller algorithms having the features as described in previous embodiments for rotating the inner sleeve 415 as well as stopping the inner sleeve 415 in a selected rotational position, such as a window-closed or window-open position. The working end 420 again has an outer sleeve window 422 that cooperates with an inner sleeve window 425 for engaging and resecting tissue.

The variation in FIGS. 10 and 11A-11C, the shaft assembly 405 differs in that the outer sleeve 410 has a distal end portion that comprises a dielectric body or housing 440 in which the outer window 422 is disposed. In one variation, the proximal 426a and medial portions 426b of the outer sleeve 410 that extend from the hub 402 comprise a thin wall, electrically conductive metal tube 428, such as a stainless steel. As will be described further below, a proximal or medial portion of the metal tube functions as an electrode indicated at 430 in FIG. 10. In a typical variation, the dielectric housing 440 comprises a ceramic material, a glass material, a polymeric material or a combination thereof. In some variations, the dielectric housing 440 can be carried within a metal support portion 442 of the metal outer tube 428 which extends underneath or partly surrounding the dielectric housing 440.

Figure 11A:
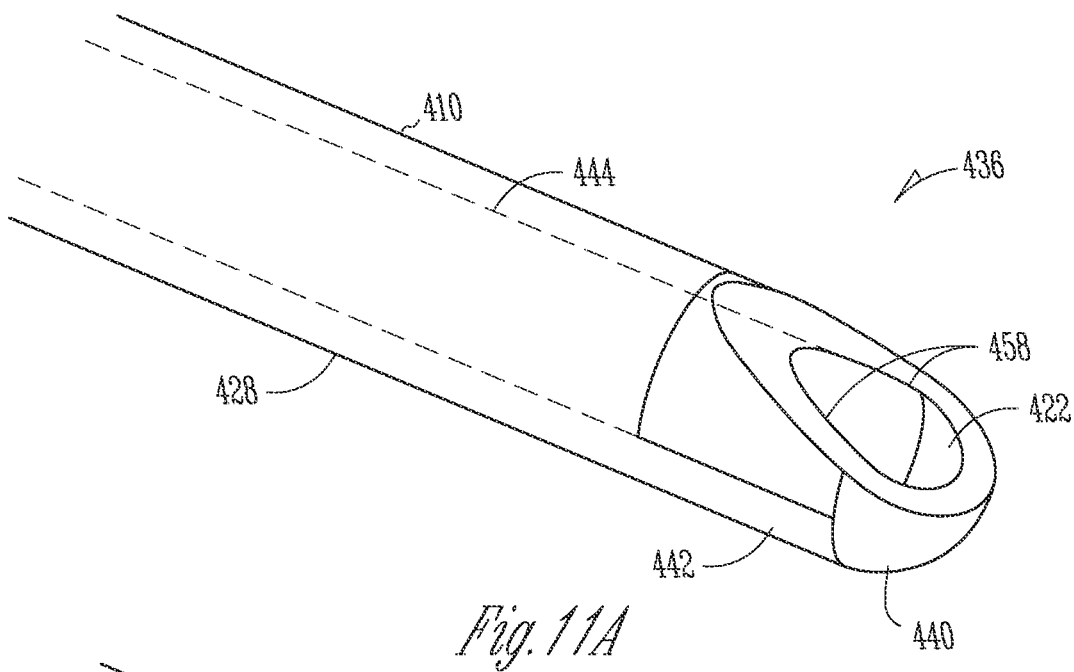
FIG. 11A is perspective view of the working end of the outer sleeve of the probe of FIG. 10 separated from the inner sleeve.

FIG. 11A shows the working end 436 of the outer sleeve 410 with outer window 422 separated from the inner sleeve 415. It can be seen that passageway or bore 444 extends through the outer sleeve 410 and the dielectric housing 440 in which the concentric inner sleeve 415 is rotationally disposed.

Figure 11B:
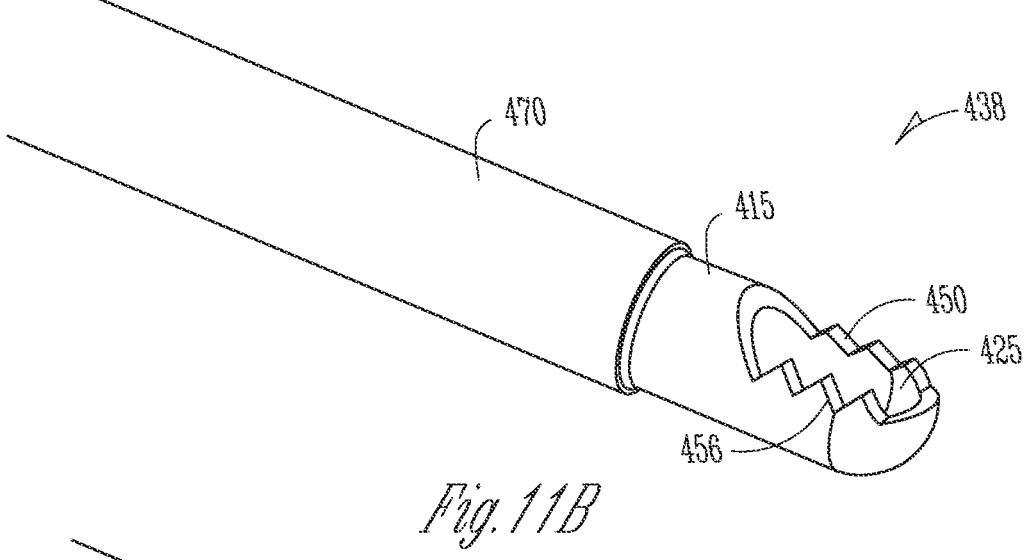
FIG. 11B is perspective view of the working end of the inner sleeve of the probe of FIG. 10 with the inner sleeve window facing upward.
Figure 11C:
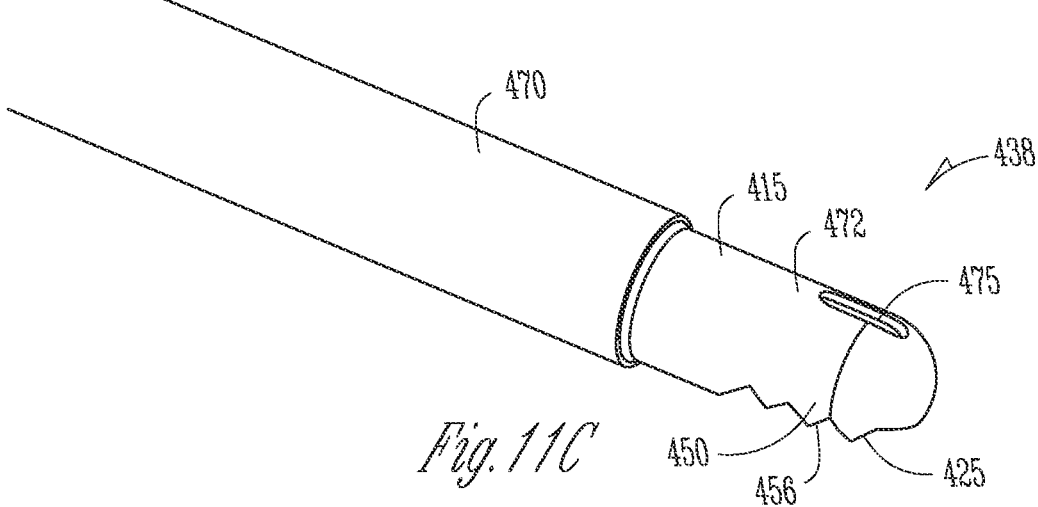
FIG. 11C is perspective view of the working end of the inner sleeve of FIG. 11B with the inner sleeve window facing downward.

FIG. 11B shows the working end 438 of the inner sleeve 415 separated from the outer sleeve 410 of FIG. 11A in a first position in which the inner sleeve window 425 is facing upwardly. FIG. 11C illustrates the same inner sleeve 415 rotated 180° so that the inner sleeve window 425 is facing downward. As can be seen in FIGS. 11B-11C, the inner sleeve 415 comprises a thin wall metal tube of a conductive material, such as stainless steel, which then can function as an electrode indicated at 450. Thus, the working end 438 of the inner sleeve 415 which carries the inner window 425 comprises electrode 450 which is configured with a close rotational fit in the bore 444 of the dielectric housing 440 so that the inner window edges 456, with optional teeth, and the edges 458 outer sleeve window and act like scissors for shearing or resecting tissue, either mechanically or electro-surgically, as will be described further below. Still referring to FIGS. 11A and 11B, the inner sleeve 415 is a thin layer 470 of an insulating polymer such as a heat shrink tubing or the parylene coating to electrically insulate the outer surface of inner sleeve 415 from the inner surface of the metal outer sleeve 428.

Figure 10:
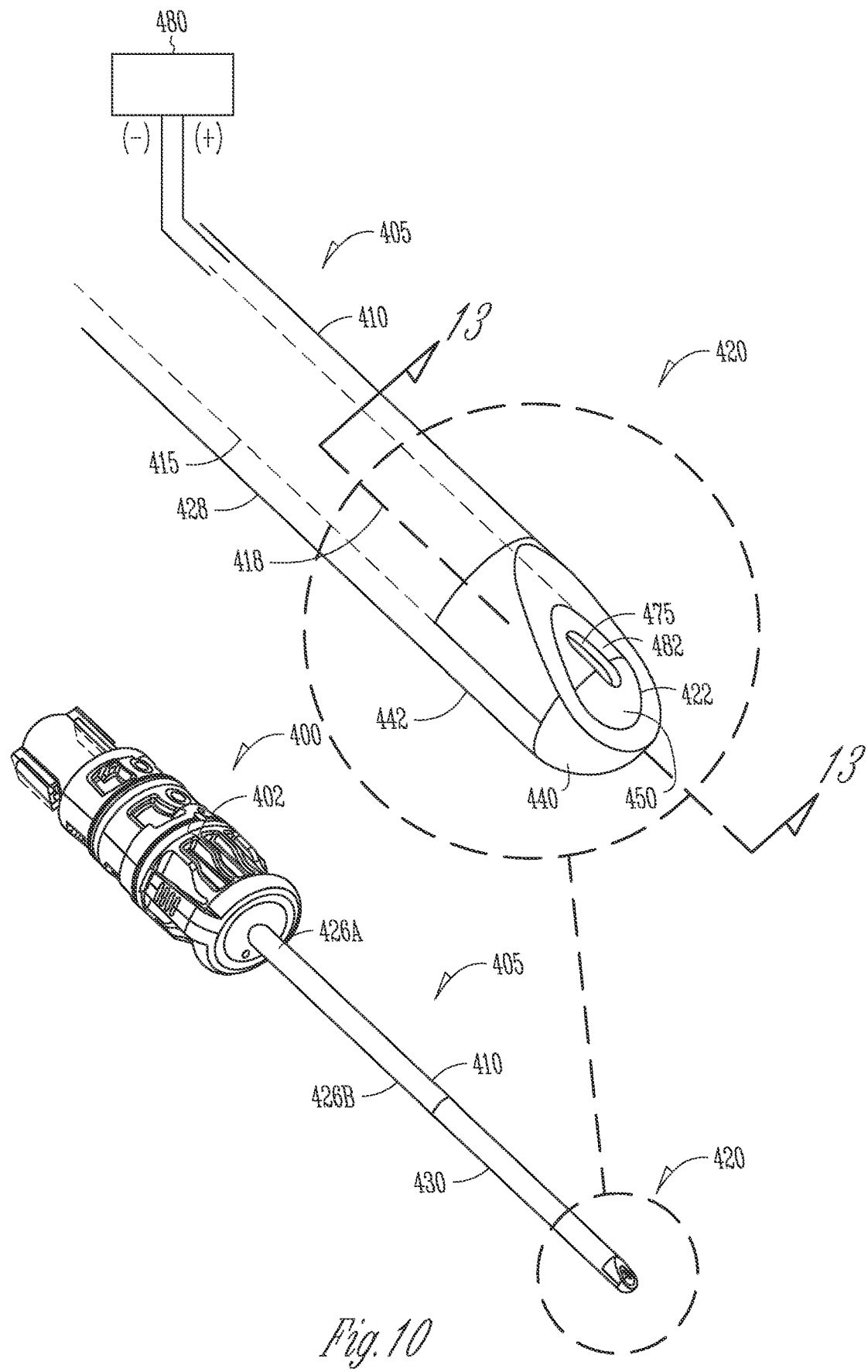
FIG. 10 is a perspective view of another variation of a probe that shows a motor-driven, rotating inner cutting sleeve that comprises an electrode and outer sleeve carrying a distal dielectric housing.

In another aspect of the invention as can be seen in FIGS. 10 and 11C, the back side 472 of the inner sleeve 415 opposing the inner sleeve window 425 has at least one opening 475 that is provided for fluid outflows therethrough when the inner sleeve 415 is rotated relative to the outer sleeve 410 to a window-closed position (see FIG. 1).

FIG. 12 illustrates the dielectric or ceramic housing 440 with the outer sleeve 415 in phantom view. It can be seen that the dielectric housing 440 has a recessed portion 476 in which the distal end 477 of outer sleeve 410 surrounds and supports the dielectric housing 440. The thickness of the wall of the dielectric housing around the window 422 can range from about 0.05" to 0.20".

Figure 13:
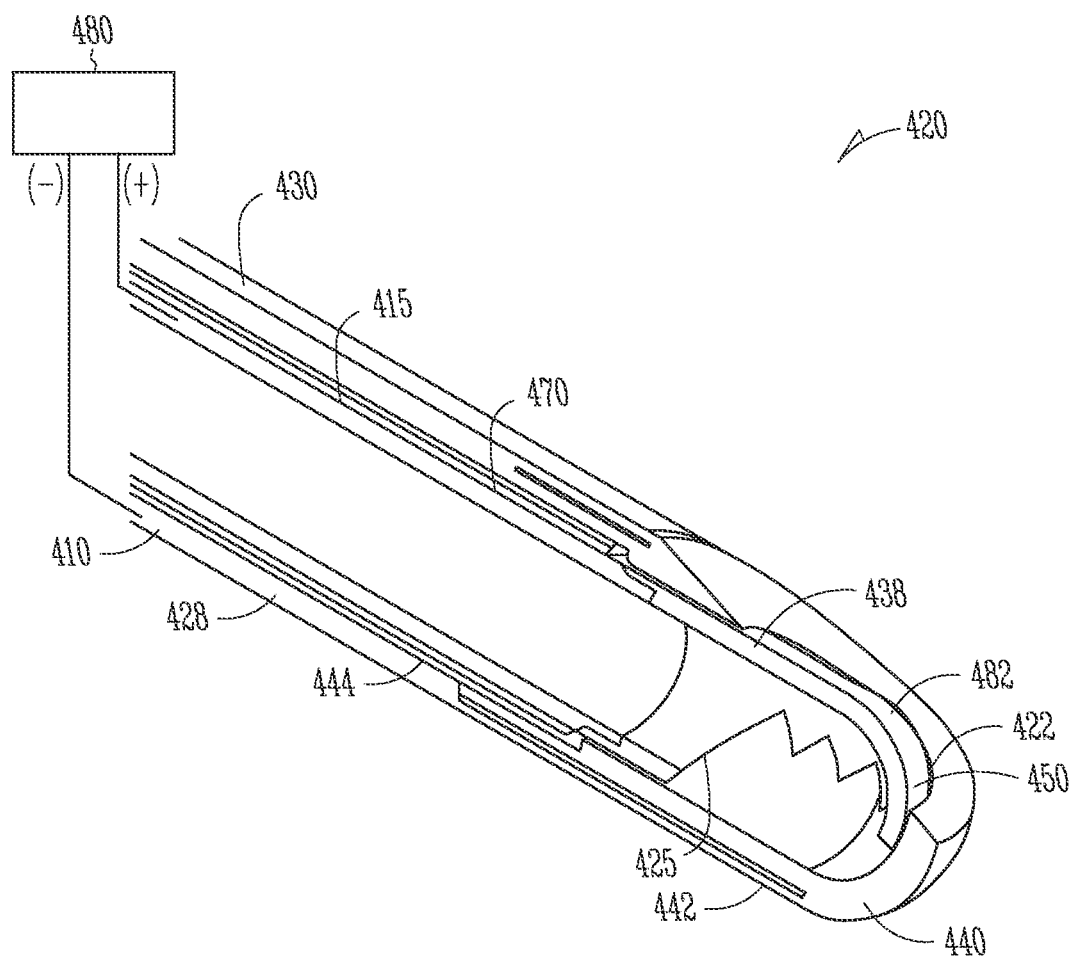
FIG. 13 is a sectional view of the working end of FIG. 10 taken along line 13-13 of FIG. 10.

FIG. 13 is a longitudinal sectional view of the working end 420 of the probe of FIGS. 10-11C which shows the working end 420 window-closed position. It can be seen that the working end 438 of the inner sleeve 415 is in close tolerance with bore 444 in outer sleeve and dielectric housing 440 so that rotation of inner sleeve 415 can shear tissue engaged by the inner sleeve and outer sleeve windows 422, 425. FIG. 13 further illustrates the support portion 442 of the metal outer sleeve 428 that extends underneath the ceramic housing 440. In addition, FIG. 13 also shows the thin insulating layer 470 that surrounds the inner sleeve 415 to electrically insulate the inner sleeve from the metal outer sleeve 428.

Still referring to FIG. 13, an RF source 480 is coupled to both the inner sleeve 410 and the outer sleeve 415 to provide for electrosurgical functionality. The RF source 480 is capable of delivering an average of at least 100 W, or at least 200 W, or at least 300 W or at least 400 W to ignite a plasma over the exposed outward or exterior surface 482 of the inner sleeve 415 in the window-closed position as shown in FIG. 10. Typically, the outward surface 482 of the inner sleeve 415 in the window-closed position is less than 15 mm$^2$, less than 10 mm$^2$ or less than 8 mm$^2$. In operation, it can be thus understood that rotation of the inner sleeve 415 in the outer sleeve 410 in a first mode of operation can mechanically shear tissue engaged by the windows 422 and 425 or in a second mode of operation to electrosurgically resect tissue. That is, the inner sleeve can rotate and shear tissue contemporaneously the RF source 480 delivers the cutting current to the inner sleeve to energize the edges of the inner sleeve window 425 which can create a plasma to shear tissue, or to assist in shearing tissue.

In general, a resecting probe or treatment device corresponding to the invention comprises shaft assembly 405 having an outer sleeve 410 and a rotatable inner sleeve 415 co-axially received in a bore 444 in outer sleeve, wherein the inner and outer sleeves have respective inner and outer cutting windows, 422 and 425, with cooperating cutting edges in distal portions thereof, and wherein the distal portion of the outer sleeve that carries the cutting window 422 comprises a dielectric housing 440 and the distal working end 438 of the inner sleeve 415 that carries the inner cutting window 425 comprises an RF electrode 450.

In this variation, the dielectric material of the dielectric housing can comprises at least one of a ceramic, a glass and a polymer. For example, the ceramic material can be selected from the group consisting of alumina, zirconia, silicon nitride, yttria-stabilized zirconia, magnesia-stabilized zirconia, ceria-stabilized zirconia and zirconia toughened alumina.

The probe of FIG. 10 further comprises a motor configured to selectively rotate in the inner sleeve in first and second rotational directions, with the radiofrequency (RF) source 480 coupled to the electrode. Further, a controller is operatively coupled to the motor and to the RF source.

In general, the controller includes an algorithm for stopping the motor to position the inner sleeve in a window-closed position or a window-open position. Further, the controller is configured to selectively operate in (i) a first mode in which the motor rotates or oscillates the inner sleeve with the RF electrode not energized for mechanically cutting tissue; (ii) a second mode in which the motor rotates or oscillates the inner sleeve with the RF electrode energized for electrosurgically cutting tissue; (iii) a third mode in which the inner sleeve is stationary in the window-closed position and the RF electrode is energized for applying coagulative or ablative energy to tissue; and (iv) a fourth mode in which the inner sleeve is stationary in the window-open position and the RF electrode is energized for applying coagulative or ablative energy to tissue.

Figure 14:
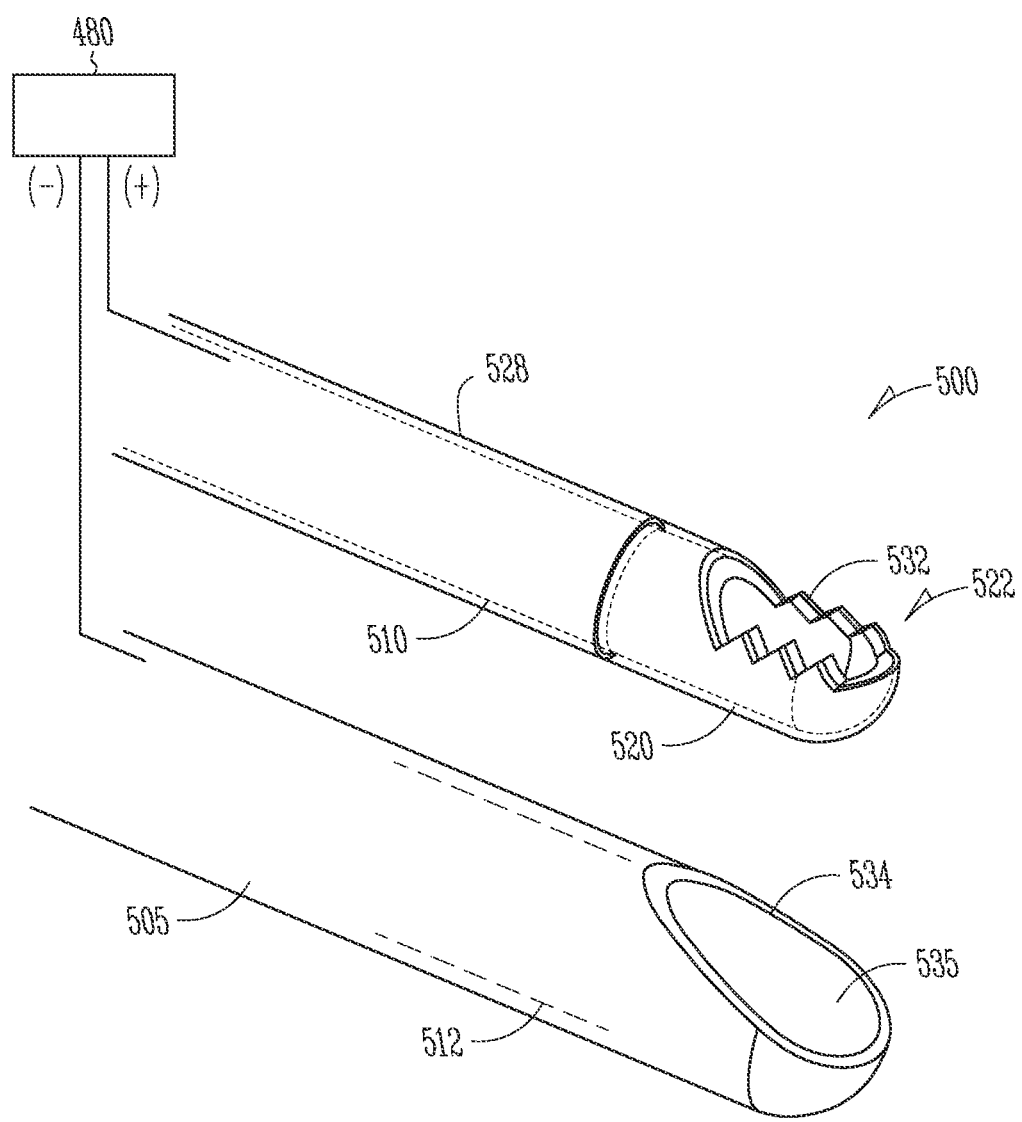
FIG. 14 illustrates another variation of a working end that includes an outer sleeve and inner sleeve.

FIG. 14 illustrates another variation of a working end 500 that includes an outer sleeve 505 and inner sleeve 510 that is adapted to rotate in bore 512 of the outer sleeve. In this variation, the outer sleeve 505 comprises a conductive metal tube without the ceramic housing as in the previous variation of FIGS. 10 and 11A. In this variation, the dielectric component that separates the conductive inner sleeve 510 from the conductive outer sleeve comprises a dielectric coating or layer 520 on the distal end 522 of the inner sleeve 510 and the polymer coating 528 over the proximal and medial portions of the inner sleeve 510. The dielectric material 520 at the distal end 522 of the inner sleeve can be a ceramic or a glass material that can be configured with sharp edges 532 so as to provide sharp, durable cutting edges 532 for cooperating with the edges 534 of the outer sleeve window 535. In all other respects, the variation of FIG. 14 can operate is the same manner as the variation described above in FIGS. 10-13.

Figure 15:
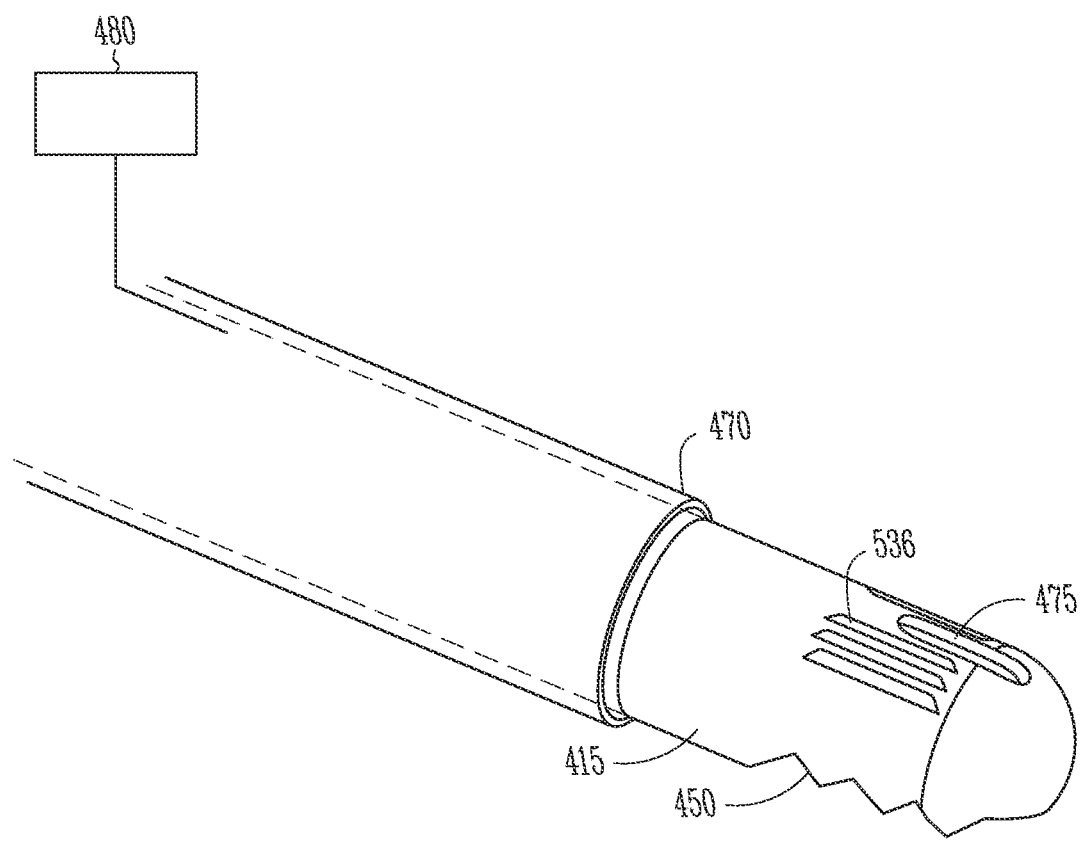
FIG. 15 is a perspective view of a working end of a motor-driven, rotating inner sleeve similar to that of FIGS. 11B-11C with abrasive cutting features for abrading bone.

FIG. 15 is a perspective view of a working end of a motor-driven, rotating inner sleeve similar to that of FIGS. 11B-11C with abrasive cutting features or sharp edges 536 for abrading bone. Thus, another mode of operation can be to rotate the inner sleeve at high speeds to use the abrasive features 536 to cut or abrade bone, typically without RF current being applied to the electrode surface. In some methods, and RF current can be applied to the electrode surface while abrading hard tissue or cauterizing purposes.

Figure 16:
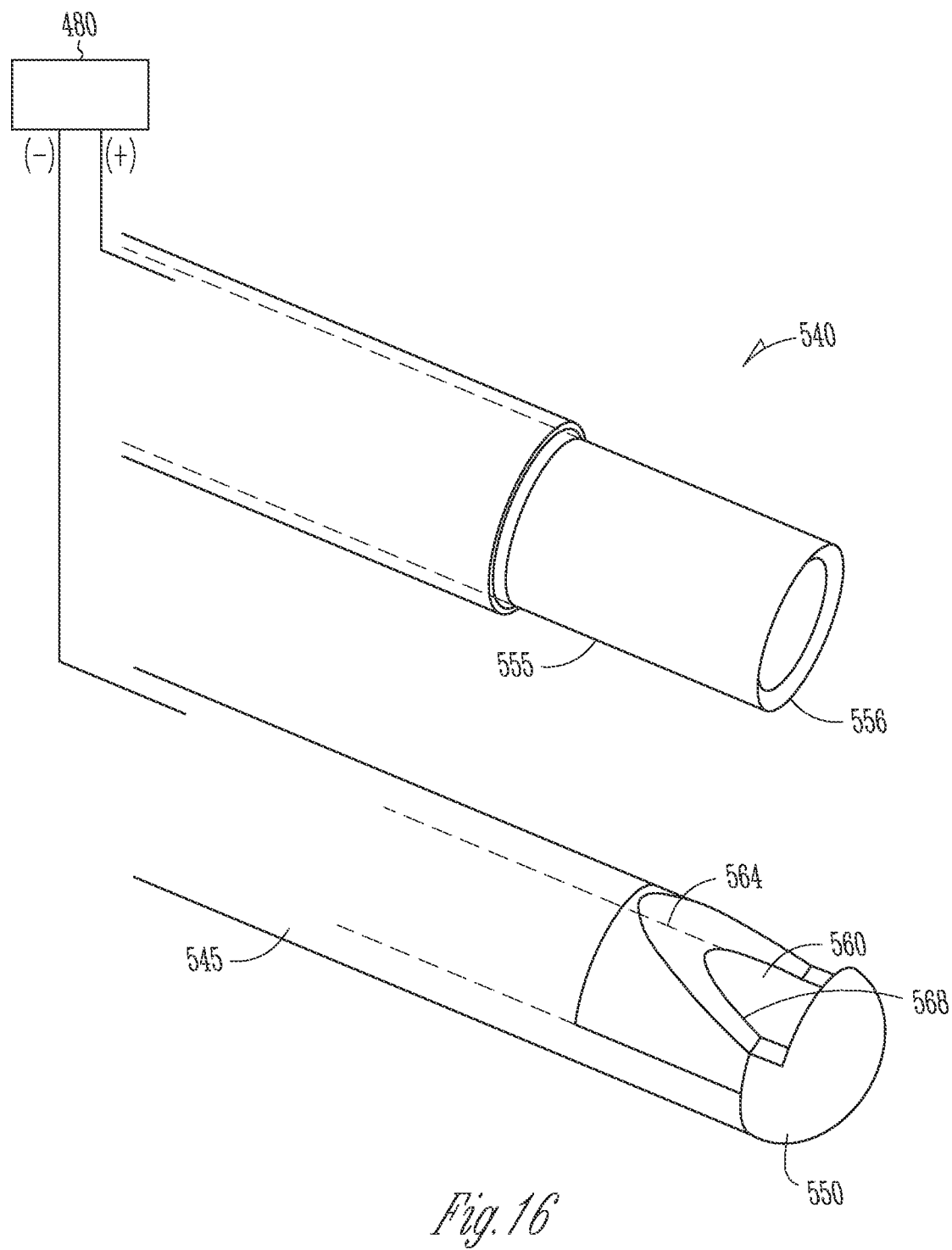
FIG. 16 is a perspective view of a working end of another variation of a probe that shows a motor-driven, reciprocating inner sleeve comprising an electrode that reciprocates in a dielectric housing carried by the outer sleeve.

FIG. 16 illustrates another variation of working end 540 that operates under similar principles to that of the variation of FIG. 10 wherein the outer sleeve 545 carries a distal dielectric or ceramic housing 550 and a concentric inner sleeve 555 with cutting edges 556 is adapted to move relative to the outer sleeve window 560 in the dielectric housing 550. However, in this variation, the inner sleeve 555 is adapted to reciprocate rather than rotate. In other respects, the cutting edges 556 of the inner sleeve 555 are configured with a close fit to the bore 564 in the dielectric housing 550 such that the inner sleeve cutting edges 556 and the edges 568 of outer sleeve window 560 shear tissue engaged by the window 560. As described in previous embodiments, an RF source 480 is operatively coupled to both the inner and outer sleeves 545 and 555 to allow for electrosurgical cutting. In use, the reciprocation of inner sleeve thus can resect tissue mechanically or electrosurgically as described above.

Figure 17:
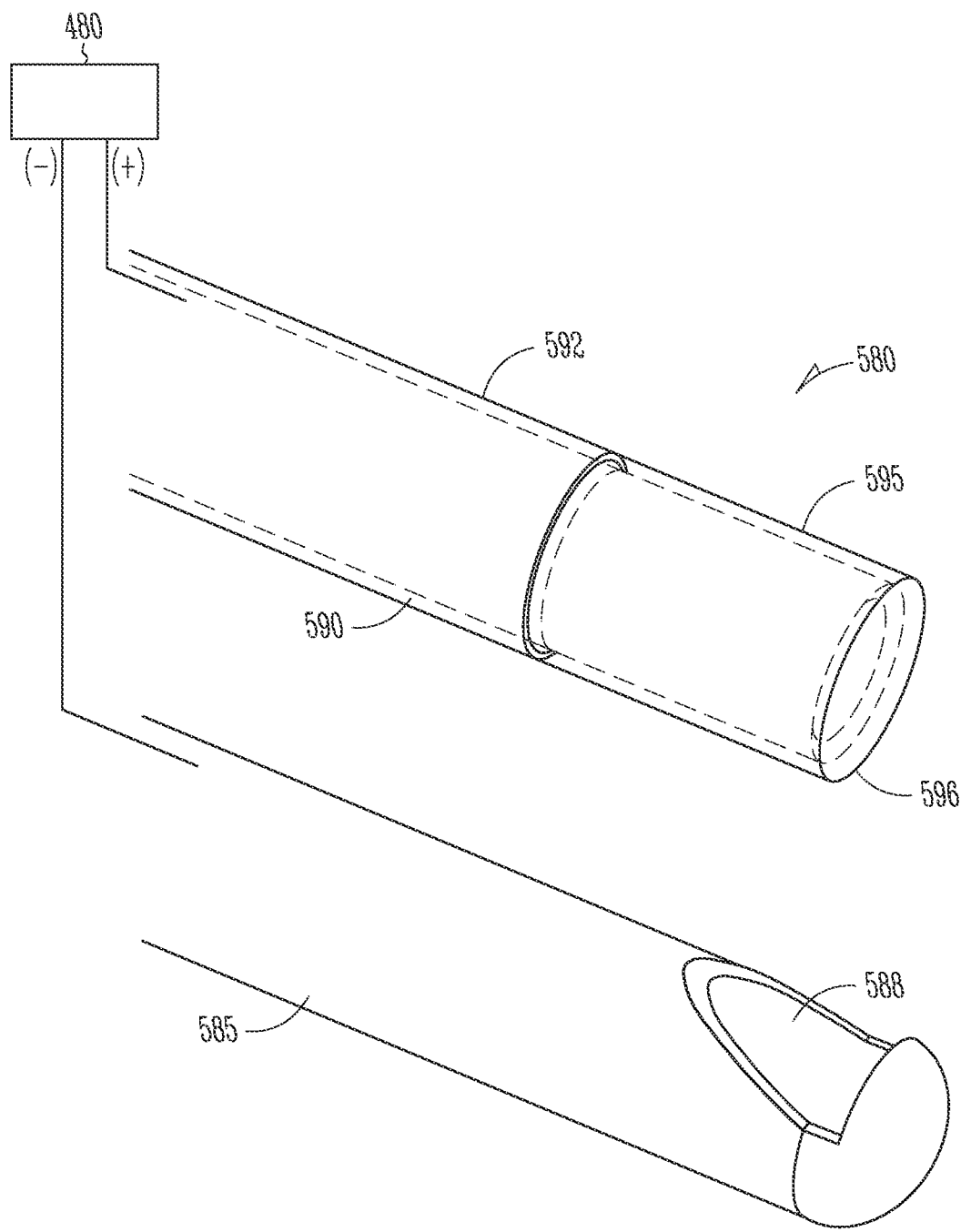
FIG. 17 is a perspective view of a working end of another variation of a probe that shows a reciprocating inner sleeve with a ceramic or glass cutting edge surrounding an electrode sleeve that reciprocates in a metal outer sleeve.

FIG. 17 illustrates another variation of working end 580 that again is similar to that of FIGS. 14 and 15. In this variation, the outer sleeve 585 comprises a thin wall conductive metal with window 588 therein. The inner sleeve 590 comprises a metal sleeve encased in an insulative polymer 592 and a distal ceramic or glass portion 595 that functions as an electrical insulator as well as providing a cutting edge 596. In this variation, the inner sleeve 590 again is adapted to reciprocate rather than rotate in the outer sleeve window 588. Again, an RF source 480 is operatively coupled to both the inner and outer sleeves 585 and 590 to allow for electrosurgical cutting. In use, the reciprocation of inner sleeve and thus can resect tissue mechanically or electrosurgically as described above.

Figure 18:
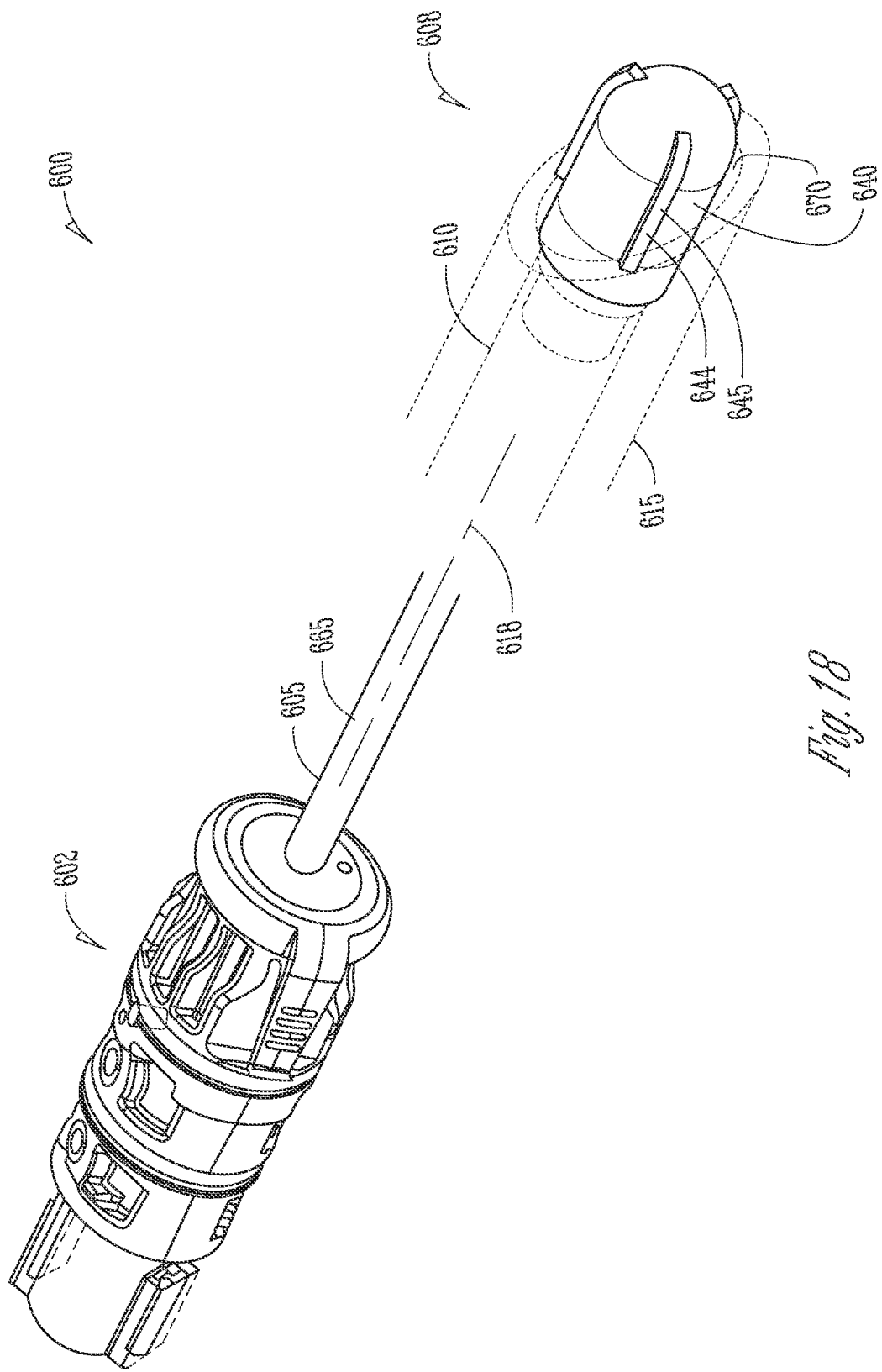
FIG. 18 is a perspective view of another variation of a probe that has a rotating inner sleeve that carries a working end including a cutting member having a plurality of burr elements extending radially outwardly from a dielectric of the cutting member, wherein the burr provides for both mechanical and electrosurgical cutting. A distal end of the inner sleeve is shown in full line and a proximal portion of the inner sleeve and a surrounding outer sleeve are shown in broken line.
Figure 19:
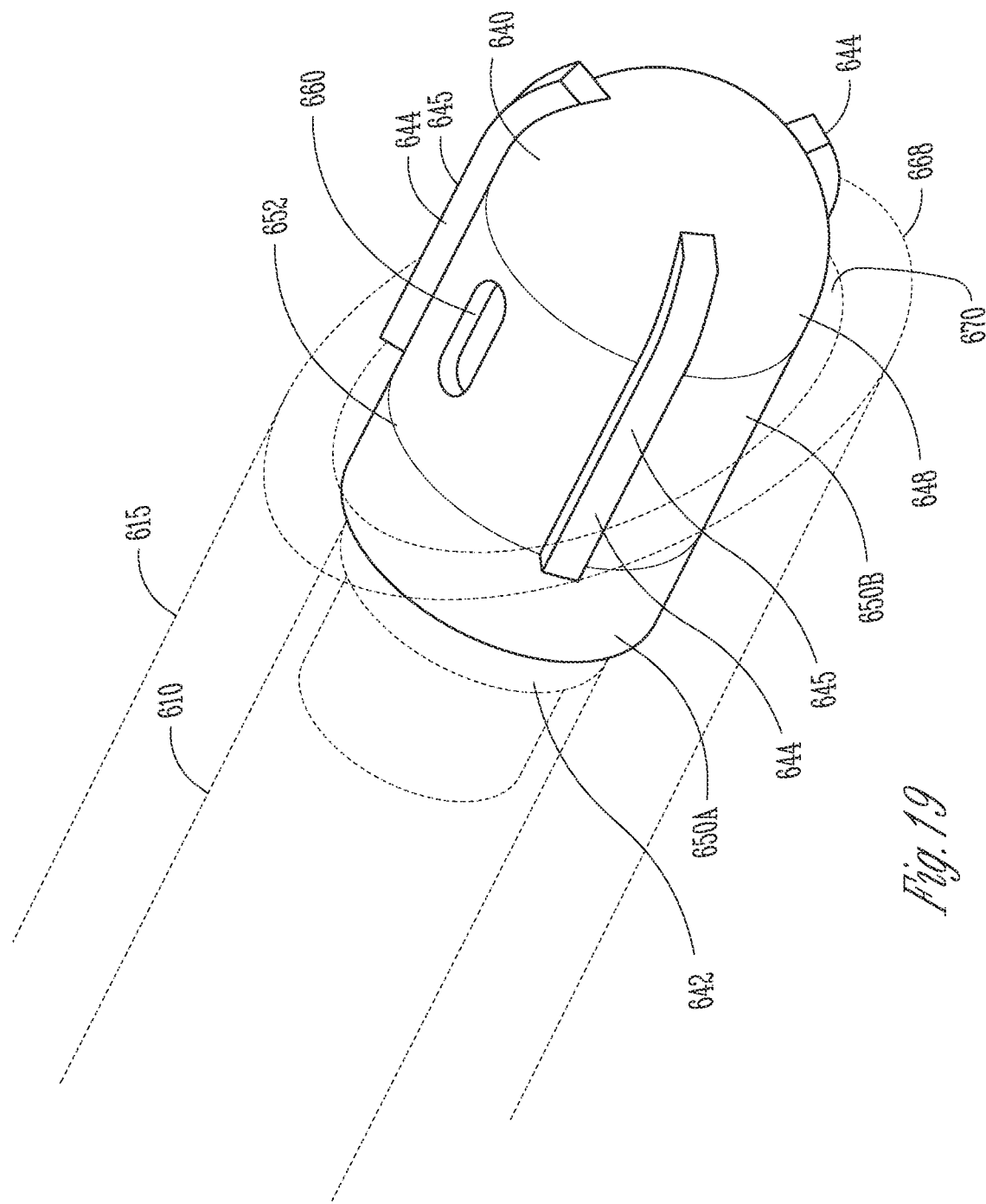
FIG. 19 is an enlarged view of the working end of FIG. 18.
Figure 20:
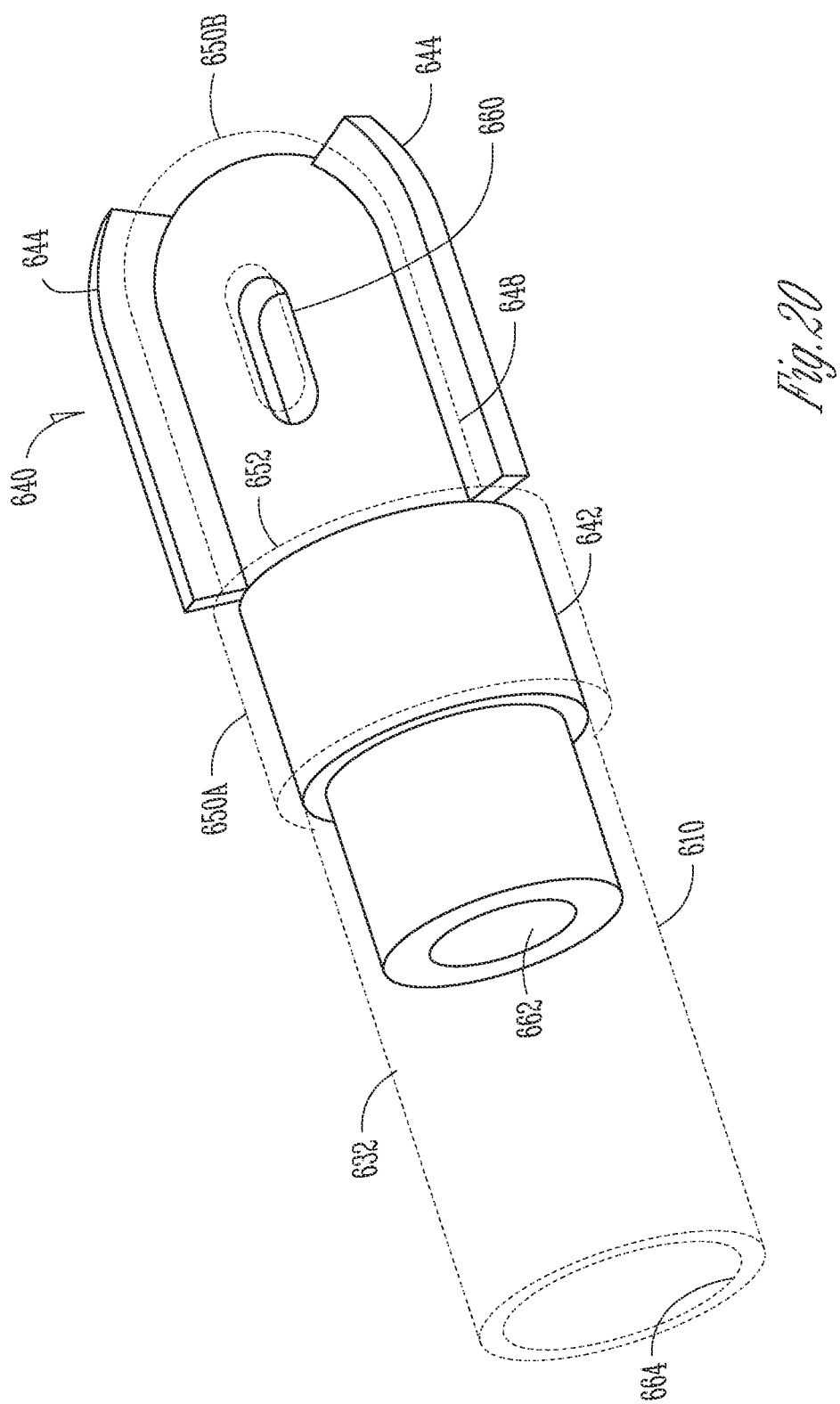
FIG. 20 is a view of the distal end of the inner sleeve of FIG. 18 removed from the outer sleeve showing an interior channel therein that communicates with apertures in the cutting member.

Now turning to FIGS. 18-20, an arthroscopic probe 600 of the present invention has a proximal hub 602 coupled to an elongated shaft assembly 605 with a working end 608 at its distal end, similar to the embodiment shown in FIGS. 1 and 3A-3B previously. The shaft assembly 605 comprises a first or inner sleeve 610 and a second or outer sleeve 615 that extends coaxially over the inner sleeve along a longitudinal axis 618 to the working end 608. The proximal hub 602 may be of the type shown in FIG. 10 and is adapted for coupling to the hand piece and motor drive, as previously disclosed. The motor drive is typically operated by a controller operating with algorithms having the features as described in previous embodiments for rotating the inner sleeve 610.

As shown in FIGS. 18-20, the inner sleeve 610 of the shaft assembly 605 typically has a proximal portion formed of a thin-wall tubular conductive member 632 (FIG. 20) attached at its distal end to the distal cutter member 640. The distal cutter member 640 typically comprises a metal core 642, usually a cylindrical or other tubular member with an interior channel 662 therethrough. Burr elements 644 are formed or welded on an exterior surface of the metal core 642, where the burr elements 644 typically comprise linear blades aligned axially over an the exterior surface of the metal core 642 and where the burr elements can be coupled to an RF power supply to serve as active electrodes.

As best seen in FIG. 20, a dielectric cover 648 (e.g., a ceramic, glass or polymer housing shown in broken in FIG. 20), is disposed over the metal core 642. In one variation, the dielectric cover 648 can comprise a proximal component 650A and a distal component 650B that abut along an interface 652 and can be coupled by a bonding or using a filler material. Thus, in this variation, the strength and durability of the burrs 640 are increased by the structural elements e.g., the core 642 and burr edges 644 are metal encased in the dielectric portion which acts as a non-structural housing 648 and is not subject to loading during high speed rotation of the burr 640.

As can further be seen in FIGS. 19-20, the distal cutting member 640 has a plurality of windows 660 therein that communicate with the interior channel 662 in the burr and an extraction channel 664 in the inner sleeve 610 (FIG. 20). In one variation, a portion of the exterior surface of the outer sleeve 615 comprises a return electrode 665 (FIG. 18). A can be understood from FIG. 19, a cut-out 670 is formed in a distal end 668 of the outer sleeve or member 615. The cut-out 670 exposes the burr and can have any form or shape, typically being a chamfered or angled cut across the distal end of the outer sleeve 615. The probe 600 is adapted to be driven at high rotational speeds by the motor drive unit to cut bone and hard tissue, for example at rotational speeds ranging from 100 RPM to 20,000 RPM.

In order to electrosurgically enhance resection, a plasma may be ignited around the burr elements 645 while rotating the distal cutter member 640 in saline. Usually, the burr elements will have surfaces areas optimized for igniting plasma at rotational speeds above 1,000 RPM with powers below 400 W. Typically, the total electrode surface area in the plurality of bur members 644 will be less than 50 mm$^2$ and often less than 25 mm$^2$. In some variations, the total electrode surface area in the burr edges 644 is less than 15 mm$^2$. Typically, the power of the RF source and the electrode surface area are adapted to provide for plasma ignition at rotational speeds ranging from 100 RPM to 20,000 RPM.

In general, the probe can be used in a first mode of operation in which the inner sleeve 610 and cutter 640 rotate without RF current to cut tissue mechanically. In a second mode of operation, the inner sleeve 610 and burr 640 can rotate contemporaneously with activation of the RF source to form plasma about burr elements 645 to provide electrosurgically enhanced cutting or resection of hard tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic cutting probe, comprising:
   a proximal hub;
   an elongate shaft assembly extending distally from the proximal hub to a working end of the arthroscopic cutting probe, the elongate shaft assembly comprising an inner sleeve rotatably received in a longitudinal bore of an outer sleeve; and
   a distal cutting member located at a distal end of the inner sleeve for rotating with the inner sleeve relative to the outer sleeve, the distal cutting member comprising a tubular metal core with at least a first metal burr element formed on an outer surface of the tubular metal core, the first metal burr element projecting outwardly from the outer surface of the tubular metal core and connectable to an RF source to form an active electrode, the distal cutting member further comprising an outer dielectric cover that covers portions of the tubular metal core while leaving the first metal burr element exposed along the distal cutting member.

2. The arthroscopic cutting probe of claim 1, wherein the distal cutting member includes at least a first window that is formed through the tubular metal core and the outer dielectric cover to form a first path into an interior channel of the tubular metal core.

3. The arthroscopic cutting probe of claim 2, wherein the interior channel of the tubular metal core is open to a longitudinal passageway in the inner sleeve, and wherein a proximal end of the inner sleeve is configured to be coupled to a negative pressure source to draw a partial vacuum through the longitudinal passageway, the interior channel, and the first window.

4. The arthroscopic cutting probe of claim 2, wherein the distal cutting member includes a second window.

5. The arthroscopic cutting probe of claim 1, wherein the distal cutting member includes from 2 to 10 metal burr elements.

6. The arthroscopic cutting probe of claim 1, wherein the outer dielectric cover comprises at least one of a ceramic, polymer, glass or combination thereof.

7. The arthroscopic cutting probe of claim 1, wherein the outer dielectric cover encases a lower portion of the first metal burr element.

8. The arthroscopic cutting probe of claim 1, wherein the first metal burr element extends through portions of the outer dielectric cover that are in contact with the first metal burr element.

9. The arthroscopic cutting probe of claim 1, wherein the inner sleeve is conductive.

10. The arthroscopic cutting probe of claim 1, wherein first metal burr element comprises a linear blade portion aligned axially along the outer surface of the tubular metal core.

11. The arthroscopic cutting probe of claim 1, wherein the distal cutting member includes at least two metal burr elements that each have an upper portion exposed above the outer dielectric cover.

12. The arthroscopic cutting probe of claim 1, wherein the outer dielectric cover is molded over the tubular metal core.

13. The arthroscopic cutting probe of claim 1, wherein the outer dielectric cover comprises a coating disposed over the tubular metal core.

14. The arthroscopic cutting probe of claim 1, wherein the distal cutting member has a bullet shape with a generally hemispherical distal tip that extends distally through an open distal end of the outer sleeve.

15. The arthroscopic cutting probe of claim 1, wherein the distal cutting member includes one or more metal burr elements that each have a surface area adapted for igniting plasma at a rotational speed above 1,000 RPM.

16. The arthroscopic cutting probe of claim 1, wherein the distal cutting member includes one or more metal burr elements that each have a surface area adapted for igniting plasma at a rotational speed ranging from 100 RPM to 20,000 RPM.

17. The arthroscopic cutting probe of claim 16, wherein the one or more metal burr elements each have a surface area adapted for igniting plasma with an applied RF power of 400 W or less.

18. The arthroscopic cutting probe of claim 1, wherein the distal cutting member includes one or more metal burr elements having a total electrically conductive surface area less than 50 mm$^2$.

19. The arthroscopic cutting probe of claim 1, wherein the distal cutting member includes one or more metal burr elements having a total electrically conductive surface area less than less than 25 mm$^2$.

20. The arthroscopic cutting probe of claim 1, wherein the distal cutting member includes one or more metal burr elements having a total electrically conductive surface area less than 15 mm$^2$.

* * * * *